(12) United States Patent
Bishayee et al.

(10) Patent No.: US 9,828,326 B2
(45) Date of Patent: Nov. 28, 2017

(54) AMOORANIN COMPOUNDS AND ANALOGS THEREOF AND RELATED METHODS OF USE

(71) Applicants: Northeast Ohio Medical University, Rootstown, OH (US); Enzyme Bio Systems, Chagrin Falls, OH (US)

(72) Inventors: Anupam Bishayee, Long Beach, CA (US); Ashot Martirosian, Solon, OH (US); Anushavan Yeranosyan, Solon, OH (US)

( * ) Notice: Subject to any disclaimer, the term of this patent is extended or adjusted under 35 U.S.C. 154(b) by 108 days.

(21) Appl. No.: 14/369,339

(22) PCT Filed: Dec. 21, 2012

(86) PCT No.: PCT/US2012/071182
§ 371 (c)(1),
(2) Date: Jun. 27, 2014

(87) PCT Pub. No.: WO2013/101719
PCT Pub. Date: Jul. 4, 2013

(65) Prior Publication Data
US 2014/0357711 A1    Dec. 4, 2014

Related U.S. Application Data

(60) Provisional application No. 61/580,449, filed on Dec. 27, 2011, provisional application No. 61/703,399, filed on Sep. 20, 2012.

(51) Int. Cl.
| | | |
|---|---|---|
| *C07C 67/40* | (2006.01) | |
| *A61K 31/19* | (2006.01) | |
| *A61K 31/215* | (2006.01) | |
| *C07C 51/16* | (2006.01) | |
| *C07C 62/38* | (2006.01) | |
| *C07C 67/08* | (2006.01) | |
| *C07C 69/753* | (2006.01) | |
| *C07J 63/00* | (2006.01) | |

(52) U.S. Cl.
CPC ............. *C07C 67/40* (2013.01); *A61K 31/19* (2013.01); *A61K 31/215* (2013.01); *C07C 51/16* (2013.01); *C07C 62/38* (2013.01); *C07C 67/08* (2013.01); *C07C 69/753* (2013.01); *C07J 63/008* (2013.01)

(58) Field of Classification Search
CPC ....... C07C 67/40; C07C 69/753; C07C 51/16; C07C 62/38; C07C 67/08; A61K 31/19; A61K 31/215; C07J 63/008
USPC ................ 552/510; 514/510, 557; 435/375; 560/116; 562/498
See application file for complete search history.

(56) References Cited

U.S. PATENT DOCUMENTS

| | | | | |
|---|---|---|---|---|
| 4,559,157 | A * | 12/1985 | Smith | A45D 37/00 106/8 |
| 4,608,392 | A * | 8/1986 | Jacquet | A61K 8/0212 424/59 |
| 4,820,508 | A * | 4/1989 | Wortzman | A61K 8/26 424/59 |
| 4,938,949 | A * | 7/1990 | Borch | A61K 31/27 514/34 |
| 4,992,478 | A * | 2/1991 | Geria | A61K 8/31 424/195.18 |
| 6,369,247 | B1 | 4/2002 | Miller | |
| 2004/0147494 | A1* | 7/2004 | Potter | A61K 31/19 514/169 |
| 2006/0167097 | A1* | 7/2006 | Ramachandran | C07J 63/008 514/559 |
| 2009/0203634 | A1* | 8/2009 | Ramachandran | C07J 63/008 514/33 |

OTHER PUBLICATIONS

Hu et al. (Acta Crystallogr Sect E Struct Rep Online. May 1, 2011; 67(Pt 5): o1027).*
Chen et al. (Bioorganic & Medicinal Chemistry Letters 16 (2006) 2915-2919).*
Wen et al. (Bioorganic & Medicinal Chemistry Letters 16 (2006) 722-726).*
Gore, Ernest, Ruthenium catalysed oxidations of organic compounds, Platinum Metals Rev., 1983, 111-125, vol. 27.
Murahashi, Shun-Ichi, Ruthenium-catalyzed oxidation for organic synthesis, Modern Oxidation Methods (book), 2010, 241-275, 2nd. Edition, ISBN: 978-3-527-32320-3.

* cited by examiner

*Primary Examiner* — Sabiha N Qazi
(74) *Attorney, Agent, or Firm* — David M. Cohn; Howard M. Cohn; Karl Dresdner

(57) ABSTRACT

Methods for synthesizing amooranin (25-hydroxy-3-oxoolean-12-en-28-oic acid (AMR) and/or amooranin analogs, including amooranin methyl ester (AMR-Me), by using oleanolic acid in an oxidation process, and therapeutic uses thereof are described.

30 Claims, 13 Drawing Sheets

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagctgacgt acagcgttga                                                       20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggtagggtg tgtggaaaac                                                       20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 aggggcctttt ttgttacagg                                                      20

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
acgtcagcaa tcatcctctg                                                        20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agggtgctac gatccaccag ca                                                     22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccatggctct gctccggctc                                                        20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccatgccca ggacaagcca                                                        20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcacgccgga ggacatggtt                                                        20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgacacgtta gcggagcgga c                                                      21

<210> SEQ ID NO 10
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 10
gcgcccgctc ttagcgtact                                                      20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agacagccgc atcttcttgt                                                      20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tactcagcac cagcatcacc                                                      20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atctccacga tcaagttcac ct                                                   22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgacattctt gcatttcatg tt                                                   22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caaagagagc tcccagaacc ta                                                   22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 16
aatgagctga ttgtcaatgt gg                                                  22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcttgttggc catctttaaa tc                                                  22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acagttttga acaagtcgct ga                                                  22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagcatttgc caagaatgtt tt                                                  22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaatcgctcc accaactaag aa                                                  22
```

AMOORANIN COMPOUNDS AND ANALOGS THEREOF AND RELATED METHODS OF USE

CROSS-REFERENCE TO RELATED APPLICATIONS

This application claims the benefit of U.S. Provisional Application Nos. 61/580,449 filed Dec. 27, 2011, and 61/703,399 filed Sep. 20, 2012, the disclosures of which are expressly incorporated herein by reference.

STATEMENT REGARDING FEDERALLY SPONSORED RESEARCH

This invention was made with government support under Grant No. 1R03-CA136014-01A2 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. The ASCII copy, created on Dec. 20, 2012, is named 3358_53491_SEQ_LIST_NEOMED.txt and is 4,893 bytes in size.

TECHNICAL FIELD OF THE INVENTION

Described herein are methods for synthesizing amooranin (25-hydroxy-3-oxoolean-12-en-28-oic acid (AMR) and amooranin analogs, including amooranin methyl ester (AMR-Me), by using oleanolic acid in an oxidation process, and uses thereof in the prevention and treatment of cancers, including cancer of the breast.

BACKGROUND OF THE INVENTION

Despite tremendous advances in medicine, breast cancer remains a leading cause of death in the United States as well as the rest of the world. In view of the limited treatment options for patients with advanced stages of breast cancer, preventive control approaches, in particular chemoprevention could play an important role in therapeutic strategies to combat this disease Although previous studies have shown the anticancer potential of methyl-amooranin (AMR-Me), a derivative of amooranin (AMR), primarily in in vitro models, pre-clinical evaluation of its efficacy could not be possible due to unavailability of sufficient quantity of these compounds. Currently, there is no commercial method available for the production of AMR or AMR-Me. Medication options for breast cancer chemoprevention include tamoxifen or raloxifene. Nevertheless, therapeutic use of these two drugs is limited to selected high-risk population. There are also considerable side effects of these drugs as well as the risk of endometrial cancer or uterine cancer. In view of these, discovery of new non-toxic breast cancer chemopreventive agent will have broader and unparalleled therapeutic utilities.

SUMMARY OF THE INVENTION

In a first aspect, there is provided herein a method for synthesizing amooranin (25-hydroxy-3-oxoolean-12-en-28-oic acid (AMR) and/or amooranin methyl ester (AMR-Me) using oleanolic acid as a starting compound.

In another aspect, there is provided herein a method for synthesizing amooranin (25-hydroxy-3-oxoolean-12-en-28-oic acid (AMR) compound 12.

In another aspect, there is provided herein compositions comprising compound 12, produced according to the methods described herein.

In another aspect, there is provided herein compositions comprising compound 13, produced according to the methods described herein.

In another aspect, there is provided herein a method for preventing and treating breast cancer, comprising administering an effective amount of compound 13 (AMR-Me).

In another aspect, there is provided herein a method of using the AMR-Me composition for a preventive effect against mammary tumorigenesis without any toxic manifestations. The presently described method eliminates the need of using plant material, which is difficult to obtain and thereby remove the dependency on unreliable sources of such plant material. Also, the presently described method for synthesizing AMR-Me ensures the steady supply of this compound. In addition, the presently describe method provides a chemopreventive and therapeutic agent for other cancer types, in addition to breast cancer.

In another aspect, there is provided herein an isolated amooranin (AMR) analog compound having the following chemical structure or a pharmaceutically acceptable salt thereof:

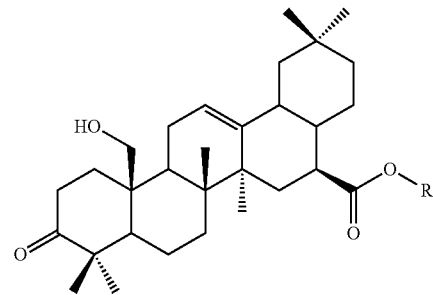

wherein R is selected from an alkyl, alkenyl, alkynyl, aryl, arylalkyl containing halogen and alkoxy, and halogen. In one embodiment, R is methyl.

The term "alkyl" can refer to a straight or branched chain alkyl moiety having from one to six carbon atoms, including for example, methyl, ethyl, propyl, isopropyl, butyl, tert-butyl, pentyl, hexyl and the like. The term "alkenyl" can refer to a straight or branched chain alkyl moiety having two to six carbon atoms and having in addition one double bond, of either E or Z stereochemistry where applicable. The term alkenyl includes for example, vinyl, 1-propenyl, 1- and 2-butenyl, 2-methyl-2-propenyl and the like. The term "alkynyl" can refer to a straight or branched chain alkyl moiety having two to six carbon atoms and having in addition one triple bond. The term alkynyl includes for example, ethynyl, 1-propynyl, 1- and 2-butynyl, 1-methyl-2-butynyl and the like. The term "aryl" can refer substituted phenyl. The term "arylalkyl" can refer substituted benzyl. The term "alkoxy" can refer to an alkyl-0-group, in which the alkyl group is as previously described. The term "alkoxy" can include a straight chain or branched alkoxy group containing a maximum of six carbon atoms, such as methoxy, ethoxy, propoxy, isopropoxy, butoxy, tert-butoxy, and the like. The term "halogen" means fluoro, chloro, bromo, and/or iodo.

As used herein, the term "analogs" refers to compounds which are substantially the same as another compound but which may have been modified by, for example, adding side groups, oxidation or reduction of the parent structure. Chemical modifications can be accomplished by those skilled in the art by protecting all functional groups present in the molecule and deprotecting them after carrying out the desired reactions. Analogs exhibiting the desired biological activity (such as induction of apoptosis, and/or cytotoxicity) can be identified or confirmed using cellular assays or other in vitro or in vivo assays.

In another aspect, there is provided herein a pharmaceutical composition comprising an isolated compound as described herein. In certain embodiments, the pharmaceutical composition further includes at least one therapeutic agent.

In another aspect, there is provided herein a method for reducing proliferation in a target cell, comprising contacting a target cell with an effective amount of the AMR analog compound (AMR-Me).

In certain embodiments, the contacting is carried out in vitro, while in certain other embodiments, the contacting is carried out in vivo.

In certain embodiments, the contacting is carried out in vivo, and wherein the contacting comprises administering the AMR analog compound to a subject.

In certain embodiments, the proliferative disorder is cancer.

In certain embodiments, the proliferative disorder is selected from the group consisting of carcinoma, lymphoma, blastoma, sarcoma, and leukemia.

In certain embodiments, the proliferative disorder is selected from the group consisting of bladder cancer, bone cancer; breast cancer, cervical cancer, colon cancer, colorectal cancer, endometrial carcinoma, esophageal cancer, gastric cancer, gastrointestinal cancer, kidney cancer, liver cancer, lung cancer including small-cell lung cancer and non-small cell lung cancer, ovarian cancer, pancreatic cancer, prostate cancer, squamous cell cancer, stomach cancer, testicular cancer, thyroid cancer, uterine cancer; and cancer of the urinary system.

In certain embodiments, the AMR analog compound is administered to the patient systemically.

In certain embodiments, the AMR analog compound is administered to the target cell locally.

In certain embodiments, the target cell is a human cell.

Various objects and advantages of this invention will become apparent to those skilled in the art from the following detailed description, when read in light of the accompanying drawings.

BRIEF DESCRIPTION OF THE FIGURES

(FIGS. 1A, 1E, 1L and 1M) DMBA control; (FIGS. 2B, 2F, 2J and 2N) AMR-Me (0.8 mg/kg body weight) plus DMBA; (FIGS. 2C, 2G, 2K and 2O) AMR-Me (1.2 mg/kg body weight) plus DMBA; and (FIGS. 2D, 2H, 2L and 2P) AMR-Me (1.6 mg/kg body weight) plus DMBA. Magnification: ×100 for H&E and apoptosis and ×200 for PCNA.

FIG. 4A. Immunohistochemical profiles of Bax (photographs a-d) and Bcl-2 (photographs e-h) proteins in the mammary tumor tissues of several groups of rats. Immunohistochemistry was carried out as described herein. Arrows indicate immuno-positive cells. Various treatment groups are: (photographs a and e) DMBA control; (photographs b and f) AMR-Me (0.8 mg/kg body weight) plus DMBA; (photographs c and g) AMR-Me (1.2 mg/kg body weight) plus DMBA; and (photographs d and h) AMR-Me (1.6 mg/kg body weight) plus DMBA. Magnification: ×200.

FIGS. 4B-4D. Quantitative analysis of Bax-immuno-positive cells (FIG. 4B), Bcl-2-immunopositive cells (FIG. 4C) and Bax/Bcl-2 ratio (FIG. 4D). Each bar represents the mean±SEM (n=4). (FIG. 4B) *P<0.001 as compared to DMBA control and (FIGS. 4C and 4D) *P<0.05 and **P<0.001 as compared to DMBA control.

(FIG. 5A): Representative Western blot analysis of Bax, Bcl-2 and Bcl-XL. Total cellular protein was separated and blotted with specific antibodies. (FIG. 5B): Representative RT-PCR analysis of apoptosis-related genes in various groups of rats. Total RNA was isolated from tumor samples, subjected to reverse transcription, and the resulting cDNA was subjected to RT-PCR analysis using specific primer sequence. The GAPDH was used as the housekeeping gene.

(FIGS. 6A and 6D) DMBA control; (FIGS. 6B and 6E) AMR-Me (0.8 mg/kg body weight) plus DMBA; and (FIGS. 6C and 6F) AMR-Me (1.2 mg/kg body weight) plus DMBA. Magnification: ×200.

(FIGS. 7A and 7B) *P<0.001 as compared to DMBA control and (FIG. 7C) *P<0.05 as compared to DMBA control.

(FIG. 9A) DMBA control; (FIG. 9B) AMR-Me (0.8 mg/kg body weight) plus DMBA; (FIG. 9C) AMR-Me (1.2 mg/kg body weight) plus DMBA; and (FIG. 9D) AMR-Me (1.6 mg/kg body weight) plus DMBA. Magnification: ×200.

(FIGS. 11A and 11B) DMBA control; (FIG. 11C) AMR-Me (0.8 mg/kg body weight) plus DMBA; and (FIG. 11D) AMR-Me (1.2 mg/kg body weight) plus DMBA. White and black arrows indicate nuclear and cytoplasmic expression of β-catenin, respectively. Magnification: ×200.

DETAILED DESCRIPTION

Definitions

Figure 1A:
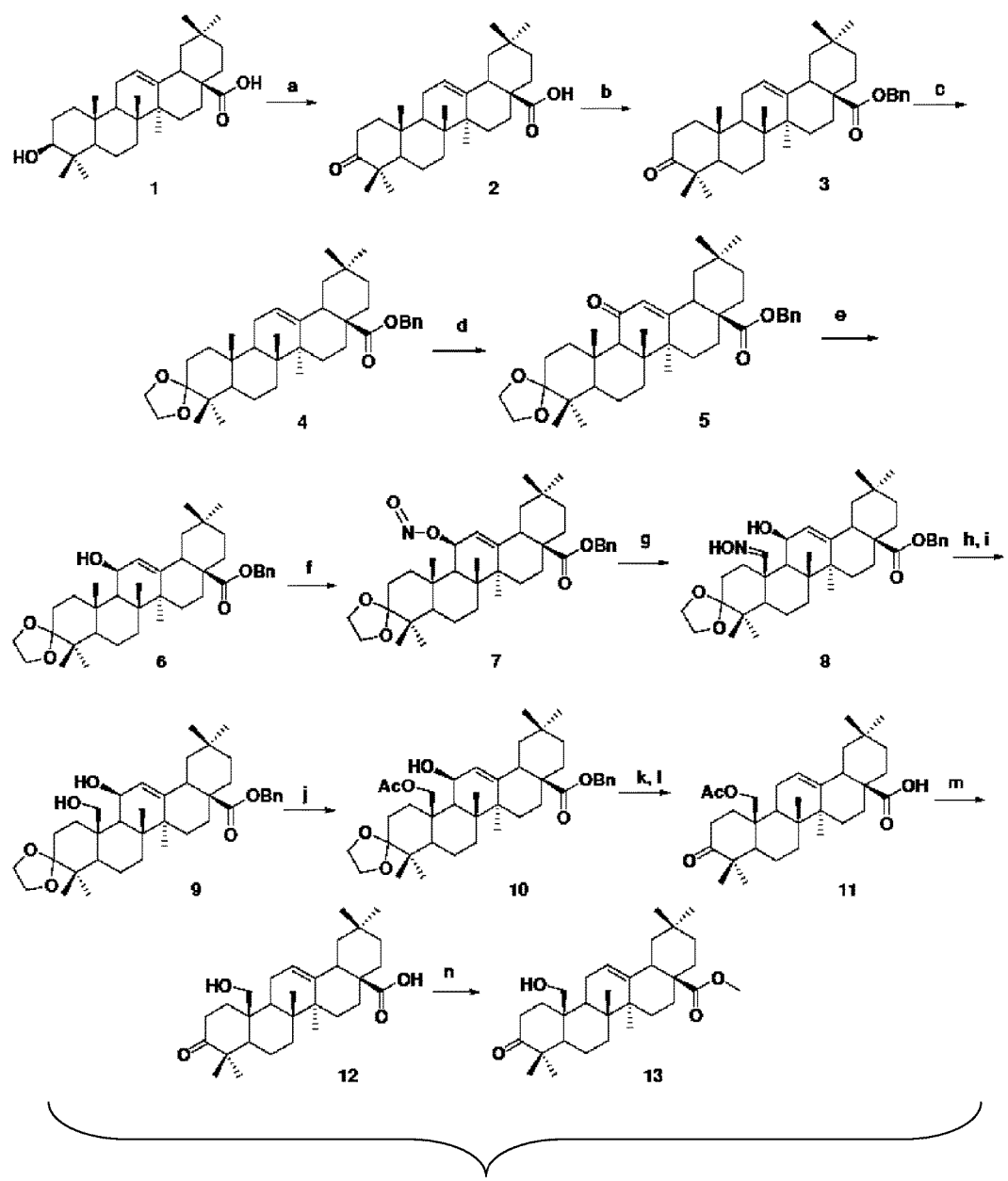
FIG. 1A. Schematic illustration of synthesis of AMR-Me in steps: (a) to (n). Reagents and reaction conditions are: in step (a) Jones' reagent, $CHCl_3$, acetone, room temperature; in step (b) Benzyl chloride, $K_2CO_3$, dioxane, reflux; in step (c) Ethylene glycol, TsOH, benzene, reflux; in step (d) $NaIO_4/RuCl_3/Bu_4NBr$, $CCl_4:H_2O/1:1$, room temperature; in step (e) $NaBH(C_2H_5)_3$, THF, room temperature; in step (f) NOCl, pyridine; in step (g) irradiated by high pressure lamp, $N_2$, room temperature; in step (h) Acetic acid, $NaNO_2$, $H_2O$, dioxane, room temperature; in step (i) $NaBH_4$, $CHCl_3/CH_3OH$; in step j) Acetic anhydride, pyridine, room temperature; in step (k) $H_2$, 10% palladium on charcoal catalyst, EtOH, room temperature; in step (l) 30% Trifluoroacetic acid, $CH_2Cl_2$, room temperature; in step (m) 2N NaOH, $CH_3OH$, reflux; and in step (n) Diazomethane, diethyl ether, 0-5° C.

For convenience, before further description of the present invention, certain terms employed in the specification, examples and appended claims are collected here. These definitions should be read in light of the remainder of the disclosure and understood as by a person of skill in the art.

Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element. The use of the word "a" or "an" when used in conjunction with the term "comprising" in the claims and/or the specification may mean "one," but it is also consistent with the meaning of "one or more," "at least one," and "one or more than one."

The term "administering" means providing a pharmaceutical agent or composition to a subject, and includes, but is not limited to, administering by a medical professional and self-administering.

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

The term "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y." The terms "comprise" and "comprising" are used in the inclusive, open sense, meaning that additional elements may be included.

The term "including" is used to mean "including but not limited to". "Including" and "including but not limited to" are used interchangeably.

The term "kit" can mean that of the compositions described herein may be comprised in a kit. The kit can also include instructions that may inform a consumer about how to use and/or administer particular compounds and/or compositions. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The term "mammal" refers to any organism classified as a mammal, including mice, rats, rabbits, dogs, cats, cows, horses and humans. In one embodiment, the mammal is a mouse. In another embodiment, the mammal is a human.

A "patient," "subject" or "host" to be treated by the subject method may mean either a human or non-human animal.

The term "plurality" means more than one.

The terms "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease or disorder is not required.

The term "treating" is art recognized and includes preventing a disease, disorder or condition from occurring in a patient which may be predisposed to the disease, disorder and/or condition but has not yet been diagnosed as having it; inhibiting the disease, disorder or condition, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected. Treating includes, without limitation, use of the subject compositions with a diagnostic for diagnostic purposes as well as a targeting moiety or an antigen.

The term "active agent" includes without limitation, therapeutic agents, diagnostics, targeting moieties, antibodies, antigens and the like.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

The terms "diagnostic" or "diagnostic agent" is any chemical moiety that may be used for diagnosis. For example, diagnostic agents include imaging agents containing radioisotopes such as indium or technetium; contrasting agents containing iodine or gadoliniums or the like.

The term "diagnosis" is intended to encompass diagnostic, prognostic, and screening methods.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of inflammation.

The phrases "systemic administration," "administered systemically," "peripheral administration" and "administered peripherally" are art-recognized, and include the administration of a subject composition or other material at a site remote from the disease being treated. Administration of a subject composition directly into, onto or in the vicinity of a lesion of the disease being treated, even if the composition is subsequently distributed systemically, may be termed "local" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, the term refers to that amount necessary or sufficient for a use of the subject compositions described herein.

When used with respect to an active agent, the term "sustained release" or "released in a sustained manner" is art-recognized. For example, a subject composition which releases an active agent over time may exhibit sustained release characteristics, in contrast to a bolus type administration in which the entire amount of the active agent is made biologically available at one time. This sustained release may result in prolonged delivery of effective amounts of the particular active agent.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human.

The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compounds of the present invention, such as the subject coordination complex, may be administered in a sufficient amount to produce a at a reasonable benefit/risk ratio applicable to such treatment.

The term "modulation" is art-recognized and refers to up regulation (i.e., activation or stimulation), down regulation (i.e., inhibition or suppression) of a response, or the two in combination or apart.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, coordination complexes of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body.

Each carrier must be "acceptable" in the sense of being compatible with the other ingredients of the supplement and not injurious to the patient.

The terms "systemic administration," "administered systemically," "peripheral administration" and "administered peripherally" are art-recognized and refer to the administration of a subject supplement, composition, therapeutic or other material other than directly into the central nervous system, such that it enters the patient's system and, thus, is subject to metabolism and other like processes, for example, subcutaneous administration.

Contemplated equivalents of the compounds described herein include compounds which otherwise correspond thereto, and which have the same general properties thereof (such as other coordination complexes comprising tethered therapeutic agents), wherein one or more simple variations of substituents are made which do not adversely affect the characteristics of the compounds of interest.

The section headings used herein are for organizational purposes only and are not to be construed as limiting the described subject matter in any way. All literature and similar materials cited in this application, including patents, patent applications, articles, books, treatises, and internet web pages are expressly incorporated by reference in their entirety for any purpose. In the event that one or more of the incorporated literature and similar materials defines or uses a term in such a way that it contradicts that term's definition in this application, this application controls.

GENERAL DESCRIPTION

In a first aspect, there is provided herein a method for synthesizing amooranin (25-hydroxy-3-oxoolean-12-en-28-oic acid (AMR) and/or amooranin methyl ester (AMR-Me) comprising using oleanolic acid in an oxidation process.

Also described herein is a method of using the AMR-Me composition for a striking preventive effect against experimentally-induced mammary tumorigenesis without any toxic manifestations. The presently described method eliminates the need of using plant material which is difficult to obtain and thereby remove the dependency on unreliable sources to obtain the key compound for research. Also, the presently described method for synthesizing AMR-Me ensures the steady supply of this compound for drug development. In addition, the presently describe method provides a chemopreventive and therapeutic agent for other cancer types, in addition to breast cancer.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

Example 1

Synthesis of Amooranin (AMR) and Amooranin Methyl Ester (AMR-Me) from Oleanolic Acid 25-Hydroxy-3-oxoolean-12-en-28-oic acid (12), amooranin (AMR), is a triterpene acid with a novel structure isolated from the stem bark of *Amoora rohituka*, a tropical tree growing wild in India. Multiple breast cancer cell lines respond to AMR in growth suppression assays. It is now believed that AMR suppresses growth factor signaling, induces cell cycle arrest, and promotes apoptosis. AMR-induced apoptosis in several human breast cancer cells are associated with the cleavage of caspase-8,-9, and -3. However, the anti-neoplastic activity of the plant-derived compound AMR is relatively weak.

An analogue of the AMR compound, AMR-Me, inhibits proliferation of several breast cancer cells with greater potency than the parent compound AMR. For example, AMR-Me in in vitro experiments reveal an astonishing potency against breast cancer MCF-7 cells with concentrations down to the nanomolar range. However, until now, it has been difficult to provide a sufficient amount of 12 for further pharmacological evaluation and study of structure-activity relationships of its derivatives, because of the scarcity of the plant in India and the low content of 12 in the plant (0.02%).

Now described herein is an efficient method for synthesizing (25-hydroxy-3-oxoolean-12-en-28-oic acid) (AMR) 12 and (25-hydroxy-3-oxoolean-12-en-28-oic acid methyl ester) (AMR-Me) 13 from oleanolic acid 1 comprising the following steps a) to n) and (see FIG. 1):

a) conducting a Jones oxidation of oleanolic acid to 3-oxoolean-12-en-28-oic acid 2;
b) introducing benzyl protecting group for the 28-carboxy group of compound 2;
c) introducing dioxolane protecting group for the 3-carbonyl group of compound 3;
d) oxidizing the compound 4 of step (c) by $NaIO_4/RuCl_3/Bu_4NBr$ system to produce compound 5 having a C-11-carbonyl group;
e) stereoselectively reducing the C-11 carbonyl group with sodium triethylborohydride in compound 5 into 11β-hydroxyl compound 6;
f) 11β-hydroxy compound 6 is an intermediate and scaffold for the Barton reaction. Hydroxy compound 6 was converted to nitrite 7 by treatment with nitrosyl chloride in pyridine;
g) irradiating unstable nitrite compound 7 under nitrogen atmosphere with a high pressure mercury lamp (400 W). Irradiations of nitrite 7 led to several byproducts along with the desired aldoxime 8;
h) treatment of aldoxime 8 with $NaNO_2$ in aqueous dioxane-acetic acid, formed mixture of aldehyde/hemiacetal-1/1. This mixture used in next step without further purification;
i) reduction of the mixture of aldehyde/hemiacetal by sodium borohydride in chloroform/methanol or methanol/NaOH systems provide C-25-hydroxylated product 9. The $^1H$ NMR spectrum of compound 9 exhibited six methyl signals, showing one methyl in the starting material was hydroxylated.
j) 25-hydroxyl in 9 was acetylated selectively by acetic anhydride in pyridine to provide 25-acetoxy product 10.

k) deprotection of the benzyl protective group of C-28 in 10 by catalytic hydrogenation with 10% palladium on charcoal. During this procedure 11-allylic hydroxyl was also removed.

l) The dioxolane protective group of C-3 was removed by 30% TFA in $CH_2Cl_2$ to provide product 11.

m) alkaline hydrolyzing 25-acetoxy group to produce compound 12 (AMR).

n) esterifying the compound 12 by diazomethane in diethyl ether at 0-5° C. to produce compound 13 (AMR-Me) (Total yield=4-5% for 15 stages).

General Experimental Procedures

Proton (1H) NMR samples are run on a Varian 300® MHz NMR spectrometer in CDCl3. J and δ values were given in hertz and ppm, respectively. Mass spectra (ESI-MS) were on ThermoLTQ Orbitrap Discovery® high resolution accurate mass MS. TLC was performed with TLC plate silica gel 60 F254 and visualized after UV irradiation. Column chromatography was done with silica gel 60 (200-300 mesh).

Example: 3-Oxoolean-12-en-28-oic Acid (compound 2) Formed by Procedure (a)

A suspension of Oleanolic acid (compound 1) (40 g, 88 mmol) in 400 ml of $CH_2Cl_2$/acetone (1:1) was cooled to 5° C., and a solution of Jones' reagent (40 ml, 1.2 equiv.) was added dropwise over 30 min maintaining the bath temperature at 5° C., and the mixture was stirred for an additional 15 min. To the reaction mixture i-PrOH (20 ml) and $H_2O$ (80 ml) were added, and the resulting mixture was stirred at room temperature for 10 min. Water (600 ml) and $CH_2Cl_2$ (400 ml) were added to the mixture and the organic layer was separated, and then washed with saturated aq. NaCl (400 ml), dried, and concentrated in vacuo. Pure 3-oxo-oleanolic acid (compound 2) was obtained by crystallization in methanol to give 34 g (85%). Compound 2: mp 178-179° C. TLC (Hexane/Acetone (4:1) Rf 0.30. 1H NMR (in $CDCl_3$): δ H 0.81 (s, 3H, $CH_3$); 0.90 (s, 3H, $CH_3$); 0.93 (s, 3H, $CH_3$); 1.02 (s, 3H, $CH_3$); 1.04 (s, 3H, $CH_3$); 1.08 (s, 3H, $CH_3$); 1.14 (s, 3H, $CH_3$); 2.36 (m, iH, H-2); 2.54 (m, 1H, H-2); 2.68 (dd, 1H, J=4.5, 13.8 Hz, H-18); 5.31 (t, 1H, J=3.3 Hz, H-12).

Example: 3-Oxoolean-12-en-28-oic Acid Benzyl Ester (Compound 3) Formed by Procedure (b)

To a solution of 3-Oxoolean-12-en-28-oic acid (compound 2) (34.0 g, 75 mmol) in 500 ml of dioxane, 38 ml of benzyl chloride (0.3 mol) and 22 g of $K_2CO_3$ (0.16 mol) were added. The mixture was refluxed for 20 h, and the solid was removed by filtration. The solvent was diluted with $CH_2Cl_2$ (1000 ml). The organic layer was washed with saturated aq. NaCl (300 ml×2), dried, and concentrated. The residue was crystallized in $CHCl_3$ and MeOH to give needle crystals (36 g, 90%). Compound 3: mp 159-160° C. TLC (Hexane/Acetone (4:1) Rf 0.5. 1H NMR (in $CDCl_3$): δ H 0.65 (s, 3H, $CH_3$); 0.90 (s, 3H, $CH_3$); 0.92 (s, 3H, $CH_3$); 1.01 (s, 3H, $CH_3$); 1.04 (s, 3H, $CH_3$); 1.08 (s, 3H, $CH_3$); 1.13 (s, 3H, $CH_3$); 2.35 (m, 1H, H-2); 2.53 (m, 1H, H-2); 2.91 (dd, 1H, J=4.0, 13.5 Hz, H-18); 5.07 (ABq, 2H, J=13.0 Hz, $OCH_2Ph$); 5.31 (br s, 1H, H-12); 7.35 (m, 5H, Ph).(m, iH, H-2); 2.54 (m, 1H, H-2); 2.68 (dd, 1H, J=4.5, 13.8 Hz, H-18); 5.31 (t, 1H, J=3.3 Hz, H-12).

Example: 3-(10,30-Dioxolane)olean-12-en-28-oic Acid Benzyl Ester (Compound 4) Formed by Procedure (c)

A suspension of compound 3 (36 g, 66 mmol), toluene (600 ml), ethylene glycol (57 ml, 0.34 mol), and p-TsOH (p-Toluenesulfonic acid, TsOH, Toluenesulfonic acid, Tosylic acid) (12.8 g, 66 mmol) was refluxed for 10 h with azeotropic removal of water with a Dean-Stark apparatus. The resulting mixture was cooled and washed with saturated aq. $NaHCO_3$ (300 ml), and the aqueous layer was extracted with EtOAc (Ethyl Acetate) (500 ml). The organic layers were combined and washed with saturated aq. NaCl, dried, and concentrated. Compound 4 (35 g, 90%) was obtained by crystallization in $CHCl_1$ and MeOH, mp 240-241° C. TLC (Hexane/Acetone (4:1) Rf 0.65. 1H NMR (in $CDCl_3$): δH 0.61 (s, 3H, $CH_3$); 0.84 (s, 3H, $CH_3$); 0.90 (s, 3H, $CH_3$); 0.92 (s, 3H, $CH_3$); 0.95 (s, 3H, $CH_3$); 0.99 (s, 3H, $CH_3$); 1.12 (s, 3H, $CH_3$); 2.90 (dd, 1H, J=4.0, 14.0 Hz; H-18); 3.90 (m, 4H, $OCH_2CH_2O$); 5.07 (ABq, 2H, J=12.4 Hz; $OCH_2Ph$); 5.28 (t, 1H, J=3.2 Hz, H-12); 7.34 (m, 5H, Ph).

Example: 3-(10,30-Dioxolane)olean-11-oxo-12-en-28-oic acid benzyl ester (compound 5) formed by Procedure (d)

Compound 4 (35 g, 60 mmol) was dissolved in $CCl_4$ (400 ml) and $H_2O$ (400 ml), and $NaIO_4$ (Sodium periodate) (65.4 g, 0.3 mol), $Bu_4NBr$ (Tetra-n-butylammonium bromide) (39.3 g, 0.122 mol) and $RuCl_3$ (Ruthenium chloride) (2.54 g, 12.3 mmol) were added. After stirring at room temperature for 24 h, the mixture was filtrated. The organic layer was separated, washed with saturated aq. NaCl (300 ml) and concentrated. Compound 5 (25 g, 70%) was obtained by crystallization in $CHCl_3$ and MeOH, mp 225-227° C. TLC (Hexane/Acetone (4:1) Rf 0.5. 1H NMR (in $CDCl_3$): δH 0.74 (s, 3H, $CH_3$); 0.84 (s, 3H, $CH_3$); 0.92 (s, 3H, $CH_3$); 93 (s, 3H, $CH_3$) 0.94 (s, 3H, $CH_3$); 1.10 (s, 3H, $CH_3$); 1.34 (s, 3H, $CH_3$); 2.36 (s, 1H, H-9); 3.02 (dd, 1H, J=4.0, 14.0 Hz; H-18); 3.94 (m, 4H, $OCH_2CH_2O$); 5.07 (ABq, 2H, J=12.4 Hz, $OCH_2Ph$); 5.63 (hr s, 1H, H-12); 7.34 (m, 5H, Ph).

Example: 3-(10,30-Dioxolane)olean-11β-hydroxy-12-en-28-oic Acid Benzyl Ester (Compound 6) Formed by Procedure (e)

Compound 5 (25 g, 41.5 mmol) was dissolved in dry THF (tetrahydrofuran) (250 ml) and cooled to −15° C., and $NaBH(C_2H_5)_3$ (Sodium triethylborohydride) (150 ml, 150 mmol, 1M in THF) was added dropwise. Reaction temperature was changed to room temperature after 30 min, and the mixture was stirred for an additional 1.5 h. 250 ml of $H_2O$ was poured, and extracted with EtOAc (250 ml×3). The organic layers were combined and washed with saturated aq. NaCl (500 ml), dried, and concentrated. The residue was purified by silica gel chromatography (Hexane/Acetone (20:1) to give compound 6 (15 g, 60%): mp 183-185° C. TLC (Hexane/Acetone (4:1) Rf 0.43. 1H NMR (in $CDCl_3$) $δ_H$ 0.80 (s, 3H, $CH_3$); 0.82 (s, 3H, $CH_3$); 0.90 (s, 3H, $CH_3$); 0.93 (s, 3H, $CH_3$); 0.94 (s, 3H, $CH_3$); 1.08 (s, 3H, $CH_3$), 1.37 (s, 3H, $CH_3$); 2.99 (dd, 1H, J=4.4, 14.0 Hz, H-18); 3.90 (m, 4H, $OCH_2CH_2O$); 4.25 (t, 1H, J=4.0 Hz, H-11); 5.08 (ABq, 2H, J=12.4 Hz, $OCH_2Ph$); 5.33 (d, 1H, J=3.6 Hz, H-12); 7.32 (m, 5H, Ph).

Example: 3-(10,30-Dioxolane)olean-11β,25-dihydroxy-12-en-28-oic Acid Benzyl Ester (Compound 9) Formed after Completion of Procedures (f), (g), (h), and (i)

Procedure (f): A stream of NOCl, generated from $NaNO_2$ (87.4 g) and 35% HCl (500 ml), was introduced to a solution of compound 6 (15 g, 25 mmol) in pyridine (100 ml) at −35° C. The mixture was stirred at −35° C. for 30 min and poured into ice-water (200 ml). The resulting suspension was extracted with EtOAc (200 ml×3), and the organic layers were combined and washed with saturated aq. NaCl (300 ml), dried, and concentrated. Procedure (g): The crude nitrite (compound 7) was used for the next photochemical transformation without further purification. The nitrite (compound 7) (16 g, 25 mmol) in dry toluene (950 ml) was irradiated with a 400 W high pressure lamp under nitrogen at room temperature for 1 h. Procedure (h): The toluene was removed in vacuo, and the unstable residue containing aldoxime (compound 8) in dioxane (120 ml), $H_2O$ (20 ml), AcOH (Acetic acid) (80 ml) was treated with 8.5 g sodium nitrite in water (25 ml) at 0° C. and left for 4 h. The mixture was extracted with EtOAc (150 ml×3), and the organic layers were combined and washed with saturated aq. $NaHCO_3$ (250 ml), and saturated aq. NaCl (250 ml), dried, and concentrated. Procedure (i): The residue was dissolved in $CHCl_3$ (150 ml) and MeOH (150 ml), 31 g (0.85 mol) of $NaBH_4$ was added and stirred for 6 h at room temperature. The solution was diluted with $CHCl_3$ (350 ml), the organic layer was washed with saturated aq. NaCl (100 ml×2), dried, and concentrated (procedure i). The residue was purified by silica gel chromatography (Hexane/Acetone (10:1). Compound 9 (5.4 g) was afforded in 36% yield in four steps. Compound 9: mp 243-245° C. TLC (Hexane/Acetone (4:1) Rf 0.2. 1H NMR (in CDCl3): δ H 0.8 (s, 3H, $CH_3$); 0.85 (s, 3H, $CH_3$); 0.9 (s, 3H, $CH_3$); 0.92 (s, 3H, $CH_3$); 0.95 (s, 3H, $CH_3$); 1.07 (s, 3H, $CH_3$); 2.99 (dd, 1H, J=3.5, 13.5 Hz, H-18); 3.75 (d, 1H, J=13.0 Hz, H-2S); 3.92 (m, 4H, $OCH_2CH_2O$); 3.99 (d, 1H, =13.0 Hz, H-2S); 4.25 (t, 1H, J=4.0 Hz, H-11); 5.07 (ABq, 2H, J=12.5 Hz, $OCH_{CIJ}$-Ph); 5.6 (d, 1H, J=4.0 Hz, H-12); 7.34 (m, 5H, Ph). ESI-MS (+): m/z 643.3 [M+Nat; ESI-MS (−): m/z 6S5.3 $[M+Cl]^-$.

Example: 3-(10,30-Dioxolane)olean-11β-hydroxy-25-acetoxy-12-en-28-oic Acid Benzyl Ester (Compound 10) Formed by Procedure (j)

A solution of compound 9 (5.4 g, 8.7 mmol) in $CHCl_3$ (50 ml) and pyridine (75 ml) was treated with $Ac_2O$ (Acetic anhydride) (2.0 ml, 19.6 mmol) at room temperature for 24 h. The solution was diluted with $CHCl_3$ (350 ml), the organic layer was washed with saturated aq. $NaHCO_3$ (100 ml), saturated aq. NaCl (100×2 ml), dried, and concentrated. Purification by silica gel chromatography (Hexane/Acetone (20:1) give compound 10 (4.7 g, 82%); TLC (Hexane/Acetone (3:1) Rf 0.65. 1H NMR (in $CDCl_3$): δH 0.82 (s, 3H, $CH_3$); 0.86 (s, 3H, $CH_3$); 0.90 (s, 3H, $CH_3$); 0.93 (s, 3H, $CH_3$); 1.01 (s, 3H, $CH_3$); 1.09 (s, 3H, $CH_3$); 2.06 (s, 1H, $OCOCH_3$); 2.98 (dd, 1H, J=3.9, 14.1 Hz, H-18); 3.94 (m, 4H, $OCH_2CH_2O$); 4.29 (t, 1H, J=4.0 Hz, H-11); 4.46 (d, 1H, J=12.0 Hz, H-25); 4.89 (d, TH, J=12.0 Hz, H-25); 5.07 (ABq, 2H, J=12.3 Hz; $OCH_2Ph$); 5.6 (d, 1H, J=3.9 Hz, H-12); 7.34 (m, 5H, Ph). ESI-MS (+): m/z 685.4 $[M+Nat]^+$;

Example: 3-Oxo-25-acetoxy-olean-12-en-28-oic Acid (Compound 11) Formed after Completion of Procedures (k) and (l)

Procedure (k): Compound 10 (4.7 g, 7.1 mmol) dissolved in EtOH (100 ml, pretreated with $NaHCO_3$) was hydrogenated over 10% Pd—C(palladium on charcoal catalyst) (9.5 g) at room temperature for 36 h. The reaction mixture was filtrated and concentrated. Procedure (l): The residue (3.5 g) was treated with 30% TFA (trifluoroacetic acid) in $CH_2Cl_2$ (20 ml) at room temperature for 3 h. 100 ml of saturated aq. $NaHC03$ was poured into the reaction solution, and extracted with EtOAc (200 ml×2). The organic layers were combined and washed with saturated aq. NaCl (200 ml), dried, and concentrated. The residue was purified by silica gel chromatography (PE/Acetone (10:1). 2.5 g of compound 11 was obtained in 75% yield. Compound 11:TLC (Hexane/Acetone (3:1) Rf 0.24. 1H NMR (in $CDCl_3$): δH 0.75 (s, 3H, $CH_3$); 0.90 (s, 3H, $CH_3$); 0.93 (s, 3H, $CH_3$); 0.96 (s, 3H, $CH_3$); 1.07 (s, 3H, $CH_3$); 1.17 (s, 3H, $CH_3$); 1.99 (s, 3H, $OCOCH_3$); 2.84 (dd, 1H, J=3.9, 14.1 Hz, H-18); 4.25 (d, 1H, J=12.0 Hz, H-25); 4.46 (d, 1H, J=12.0 Hz, H-25); 5.29 (t, 1H, J=3.2 Hz, H-12).

Example: 25-Hydroxy-3-oxoolean-12-en-28-oic Acid (Compound 12, AMR (Amooranin)) Formed by Procedure (m)

A mixture of 3-Oxo-25-acetoxy-olean-12-en-28-oic acid (11) 3.58 g (6.8 mmol.) and KOH (4.5 g) in water (15 ml) and methanol (45 ml) was heated under reflux for 60 min. After the mixture acidified with 10% aqueous HCl solution, it was extracted with EtOAc (100 ml three times). The extract was washed with saturated aq. NaCl (100 ml), dried over $MgSO_4$, and concentrated. The residue was purified by silica gel chromatography (Hexane/Acetone (10:1). Compound 12 (2.6 g, 80% yield) was afforded as white solid. Compound 12: 1H NMR (in $CDCl_3$): δH 0.74 (s, 3H, $CH_3$); 0.91 (s, 3H, $CH_3$); 0.94 (s, 3H, $CH_3$); 0.97 (s, 3H, $CH_3$); 1.09 (s, 3H, $CH_3$); 1.17 (s, 3H, $CH_3$); 2.85 (dd, 1H, J=3.9, 14.0 Hz, H-18); 3.49 (d, 1H, J=12.0 Hz, H-25); 4.01 (d, 1H, J=12.0 Hz, H-25); 5.30 (t, 1H, J=3.2 Hz, H-12). ESI-MS (+): m/z 493.4 $[M+Nat]^+$;

Example: 25-hydroxy-3-oxoolean-12-en-28-oic Acid Methyl Ester (Compound 13, AMR-Me) Formed by Procedure (n)

A solution 25-hydroxy-3-oxoolean-12-en-28-oic acid (12) 2.6 g (5.5 mmol) in ethyl ether (60 ml) cooled in an ice-water bath and treated with 100 ml cold ethereal Diazomethane (approximately 0.6M). After 30 min. at 0° C. excess of Diazomethane was destroyed with acetic acid and the resulting solution was washed with 4% sodium bicarbonate solution and brine, dried over MgS04, and concentrated. The residue was purified by silica gel chromatography (Petroleum Ether/Acetone 10:1). Compound 13 (2.0 g, 80% yield) was afforded as white solid. Compound 13: 1H NMR (in $CDCl_3$): δH 0.70 (s, 3H, $CH_3$); 0.89 (s, 3H, $CH_3$); 0.92 (s, 3H, $CH_3$); 0.96 (s, 3H, $CH_3$); 1.03 (s, 3H, $CH_3$); 1.13 (s, 3H, $CH_3$); 2.82 (dd, 1H, J=3.9, 14.0 Hz, H-18); 3.61 (s, 3H, $COOCH_3$); 3.85 (d, 1H, J=12.0 Hz, H-25); 4.24 (d, 1H, J=12.0 Hz, H-25); 5.31 (t, 1H, J=3.2 Hz, H-12). ESI-MS (+): m/z 507.4 [M+Nat]+.

Example 2

Breast Cancer Preventive Effect of AMR-Me in a Pre-Clinical Animal Model

Materials:
AMR-Me has been synthesized following a method as described herein. DMBA was purchased from Sigma-Aldrich (St. Louis, Mo.). Paraformaldehyde was obtained from Ted Pella (Redding, Calif.). Primary antibodies, such as mouse monoclonal Bax, Bcl-2, Bel-XL, ER-a, ER-β), cyclin D1, β-catenin and β-Actin were purchased from Santa Cruz Biotechnology (Santa Cruz, Calif.). Quick RNA® mini Prep kit was obtained from Zymo Research (Irvine, Calif.) and Verso cDNA® synthesis kit was purchased from Thermo Fisher Scientific (Waltham, Mass.).

Animals and Diet

Pathogen-free virgin female Sprague-Dawley rats (~36 days of age) were obtained from Harlan Laboratories (Indianapolis, Ind.). The animals were housed in a conventional animal facility accredited by the American Association for the Accreditation of Laboratory Animal Care. All animals were acclimatized to standard housing conditions (temperature 22±2° C., relative humidity 30-50%, and a 12-h dark-light cycle) in plastic cages (3-4 animals/cage) with solid bottom surface covered with special bedding (Cell-Sorb® Plus from Fangman, Cincinnati, Ohio) for one week before initiation of treatment. The animals had free access to a well-defined, Constant Nutrition® formula basal diet (Lab-Diet, St. Louis, Mo.) and drinking water. The entire animal study has been conducted using an animal protocol approved by the Northeast Ohio Medical University Institutional Animal Care and Use Committee (Rootstown, Ohio).

Experimental Design for Chemoprevention Study

Figure 1B:
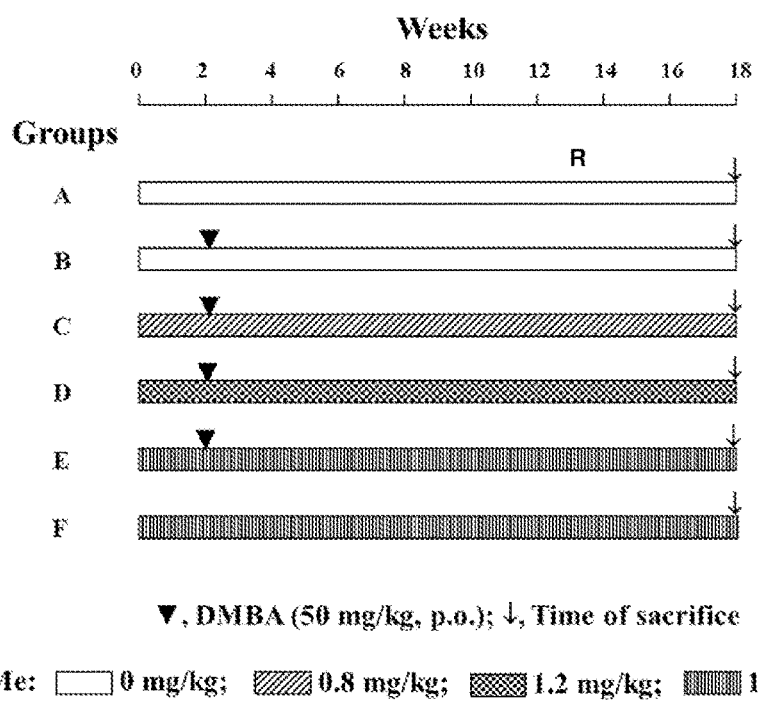
FIG. 1B. Schematic representation of the experimental protocol of mammary carcinogenesis initiated with DMBA.

Following an acclimatization period of one week, rats (~43 days of age) were randomly divided into six groups of 7-11 animals in each. Various experimental groups are depicted in FIG. 1B. Two groups (groups A and B) were maintained on the basal diet without any further treatment, whereas the remaining four groups (groups C, D, E and F) were fed with AMR-Me through oral gavage three times a week (Monday-Wednesday-Friday). AMR-Me was mixed in polyethylene glycol (Sigma-Aldrich, St. Louis, Mo.) and administered by gently securing the animal by holding the skin back of its head and delivering the drug slowly via an animal feeding needle (Popper and Sons, Inc., New Hyde Park, N.Y.) attached to a I-ml syringe (Becton Dickinson, Franklin Lakes, N.J.). This technique ensured the accurate oral dosing of the test material. Three doses of AMR-Me were used: 0.8 mg/kg (for group C), 1.2 mg/kg (for group D) and 1.6 mg/kg (for groups E and F). These three doses (low, medium and high) represent 40, 60 and 80% of calculated maximum tolerated dose (MTD) in rats, respectively. The rat MTD was calculated based on the MTD in mice (3 mg/kg/day).

Following two week of aforementioned treatment regimen, at ~57 days of age, mammary carcinogenesis was initiated in all animals belonging to groups B, C, D and E by a single administration of the mammary carcinogen, DMBA at 50 mg/kg body weight by gavage. The DMBA was dissolved in corn oil. This dose of DMBA was chosen so that substantial tumor incidence could be produced but not so high as to overwhelm the chemopreventive action of AMR-Me. Oral treatment of rats with AMR-Me in groups C, D, E and F were continued for 16 weeks following the DMBA administration (i.e., a total period of 18 weeks). Food and water intake as well as behavioral patterns were monitored daily and body weights of animals were recorded every alternate week.

Animals were palpated along the milk line twice a week starting 4 weeks following DMBA treatment to detect the presence of mammary tumors. All animals were sacrificed at 16 weeks post-DMBA treatment (i.e., 18 weeks following the start of the experiment).

Tissue Harvesting and Assays

Following an overnight fast, animals from each group were anesthetized between 09:00 and 11:00 h by intramuscular injection of 40-87 mg/kg ketamine and 5-13 mg/kg xylazine. The skin was dissected out to expose mammary tumors. The tumors (approximated spheres) were separated from mammary gland parenchyma, carefully excised, rinsed with phosphate-buffered saline (pH 7.4) to flush out any blood, blotted dry on a paper towel, weighed, and photographed. Each tumor was measured in two perpendicular directions with a vernier caliper to the nearest mm to obtain an average diameter. The representative tumor tissue as well liver and kidney were harvested and either immediately flash frozen in liquid nitrogen for molecular work or fixed in 4% paraformaldehyde. Later, serial tumor sections (~15-μm thick) were prepared using a microtome. These sections were used for histopathological assessment by hematoxylin and eosin (H&E) staining.

Immunohistochemical Analysis

Serial sections of tumor tissue were used processed for immunohistochemical analysis. Cell proliferation was studied by immunohistochemical detection of proliferating cell nuclear antigen (PCNA) as a proliferation marker. The analysis of apoptotic cells in tumor sections were performed by using TdT-FragEL™ DNA fragmentation detection assay kit (EMD Biosciences, Inc., San Diego, Calif.). The protein expression of Bax (apoptosis inducer),Bcl-2 (apoptosis repressor), ER-a, ER-β, cyclin D1 and β-catenin were determined. The immunohistochemical slides were visualized under a light microscope (BX43, Olympus, Center Valley, Pa.) and at least 1,000 cells/animal were analyzed. Results were expressed as percentage of immunopositive cells.

Western Blot Analysis

Total proteins were extracted from tumor tissues with lysis buffer (containing 20 mM HEPES, 350 mM NaCl, 500 mM EDTA, 1 mM MgCh, 20% glycerol, and 1% NP-40), boiled and separated by 4-20% gradient sodium dodecyl sulfate-polyacrylamide gel electrophoresis. The proteins were transferred to polyvinylidene fluoride membranes (Santa Cruz Biotechnology Inc., Santa Cruz, Calif.), and reacted with primary mouse monoclonal antibodies to Bax, Bcl-2, Bel-XL and β-Actin (dilution 1:200) and subsequently with anti-mouse secondary antibodies (dilution 1:1, 000) conjugated to horseradish peroxidase. The immunoreactions were detected by an enhanced chemiluminescence detection kit (Them10 Scientific, Rockford, Ill.) and relative intensities of bands on blots were quantitated by autoluminography using a Kodak digital imaging system. Normalization of Western blot was ensured by β-Actin.

Reverse Transcription-Polymerase Chain Reaction

Total RNA from 20 mg of tumor sample was extracted using Quick RNA® mini Prep kit following the manufacturer's instructions. The expression levels of apoptotic and anti-apoptotic genes were monitored by reverse transcription-polymerase chain reaction (RT-PCR) using the cDNA verso kit with a temperature scale of 42° C. for 30 min for reverse transcription, and 32 cycles of 94° C. for 30 s, 56° C. for 30 s, and 72° C. for 30 s. The RT-PCR was carried out using the primers:

BAD-F-5'-GAGCTGACGTACAGCGTTGA-3'' [SEQ ID NO: 1]

BAD-R-5'-GGGTAGGGTGTGTGGAAAAC-3'; [SEQ ID NO: 2]

BAX-F-5'-AGGGGCCTTTTTGTTACAGG-3'; [SEQ ID NO: 3]

BAX-R-5'-ACGTCAGCAATCATCCTCTG-3'; [SEQ ID NO: 4]

CASP3-F-5'-AGGGTGCTACGATCCACCAGCA-3'; [SEQ ID NO: 5]

CASP3-R-5'-CCATGGCTCTGCTCCGGCTC-3'; [SEQ ID NO: 6]

CASP7-F-5'-GCCATGCCCAGGACAAGCCA-3'; [SEQ ID NO: 7]

CASP7-R-5'-GCACGCCGGAGGACATGGTT-3'; [SEQ ID NO: 8]

PARP-F-5'-CGACACGTTAGCGGAGCGGAC-3'; [SEQ ID NO: 9]

PARP-R-5'-GCGCCCGCTCTTAGCGTACT -3'; [SEQ ID NO: 10]

GAPDH-F-5'-AGACAGCCGCATCTTCTTGT-3'; [SEQ ID NO: 11]

GAPDH-R-5'-TACTCAGCACCAGCATCACC-3'; [SEQ ID NO: 12]

ER-α-F-5'-ATCTCCACGATCAAGTTCACCT-3'; [SEQ ID NO: 13]

ER-α-R-5'-CGACATTCTTGCATTTCATGTT-3'; [SEQ ID NO: 14]

ER-β-F-5'-CAAAGAGAGCTCCCAGAACCTA-3'; [SEQ ID NO: 15]

ER-β-R-5'-AATGAGCTGATTGTCAATGTGG-3'; [SEQ ID NO: 16]

β-CATENIN-F-5'-GCTTGTTGGCCATCTTTAAATC-3'; [SEQ ID NO: 17]

β-CATENIN-F-5'-ACAGTTTTGAACAAGTCGCTGA-3'; [SEQ ID NO: 18]

18sRNA-F-5'-AAGCATTTGCCAAGAATGTTTT-3'; and [SEQ ID NO: 19]

18sRNA-R-5'-AAATCGCTCCACCAACTAAGAA-3' [SEQ ID NO: 20]

The PCR products were analyzed on 1% agarose gel and visualized by ethidium bromide staining.

Statistical Analysis

Results are presented as mean±SEM unless indicated otherwise. Significant differences among various groups were detected by one-way ANOVA. Post hoc analysis was performed by the Student-Neuman-Keuls test. The criterion for statistical significance was set at P<0.05. The commercial software SigmaStat 3.1® (Systat software, Inc., San Jose, Calif.) was used for all statistical analysis.

Results

General Observations

Figure 1C:
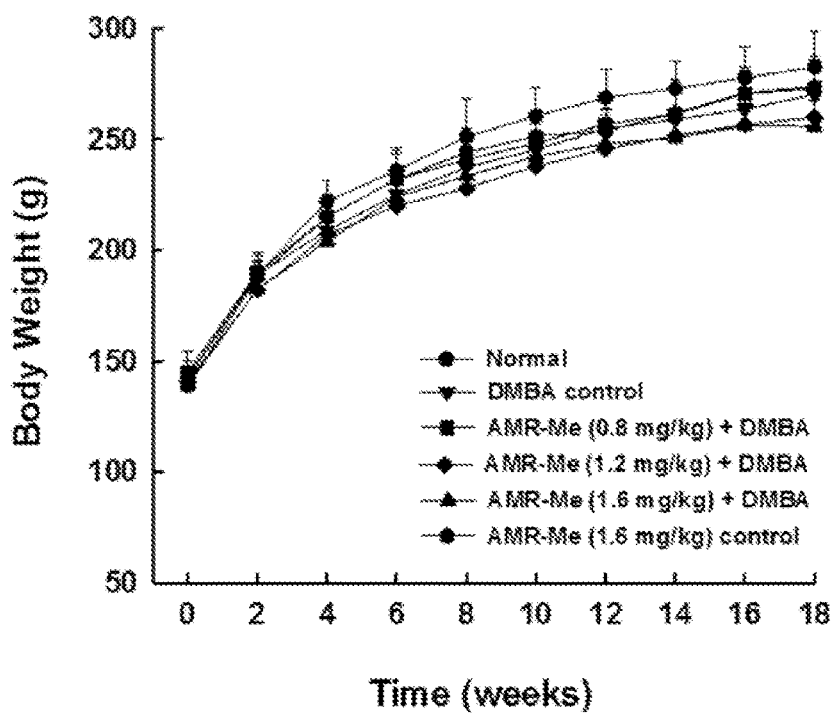
FIG. 1C. Effect of AMR-Me on body weight gain during DMBA-induced mammary tumorigenesis in rats. Each data point indicates mean±SEM. There were 7-11 animals in various groups. No significant difference in body weights was observed among various rat groups at any time point.

No difference in food and water intake was observed in various experimental groups during the entire term of the experiment. Similarly, no behavioral changes were apparent among different animal groups. The growth of animals was not affected during the entire study by any of the compounds as no significant difference was detected in the body weight between normal and any treated group at any time-point (FIG. 1C).

Effect of AMR-Me on DMBA-Induced Mammary Tumorigenesis

While there were no visible mammary tumors in normal (group A) as well as AMR-Me control (group F), macroscopic tumors of various sizes arose from the mammary glands of DMBA-treated groups. Table 1 summarizes tumor incidence, total tumor burden and average tumor weight of DMBA-initiated groups with or without AMR-Me treatment.

TABLE 1

Effect of AMR-Me on DMBA-induced mammary tumorigenesis in Sprague-Dawley rats.

| Groups | No. of rats with tumors/ total rats | Tumor Incidence (%) | Total tumor burden (g) | Average tumor weight (g) |
|---|---|---|---|---|
| B. DMBA | 9/11 | 82 | 83.3 | 20.8 ± 4.6 |
| C. AMR-Me (0.8 mg/kg) + DMBA | 5/8 | 62 | 57.5 | 11.5 ± 4.9 |
| D. AMR-Me (1.2 mg/kg) + DMBA | 2/7 | 28$^a$ | 9.6 | 3.2 ± 1.5$^b$ |
| E. AMR-Me (1.6 mg/kg) + DMBA | 2/7 | 28$^a$ | 0.8 | 0.38 ± 0.03$^b$ |

Animals from normal (group A) and AMR-Me (1.6 mg/kg) control group (group E) did not show any visible mammary tumor.
$^a$P < 0.05 compared with DMBA (group B) by Fisher's exact probability test.
$^b$P < 0.05 compared with DMBA (group B) by Student's t-test.

Oral AMR-Me at a dose of 0.8 mg/kg (group C) reduced the tumor incidence compared to the DMBA control (group B), but the result did not reach the level of statistical significance. A significantly (P<0.05) reduced tumor incidence was observed in the group that received AMR-Me at a dose of 1.2 mg/kg (group D) or 1.6 mg/kg (group E) as compared to DMBA control (group B). Oral administration of AMR-Me reduced the total tumor burden in various DMBA-induced groups in a dose-responsive fashion. The average tumor weight was found to be smaller in all AMR-Me treatment groups, but a statistically significant (P<0.05) result was observed in groups D and E compared to group B.

Figures 2A, 2P:
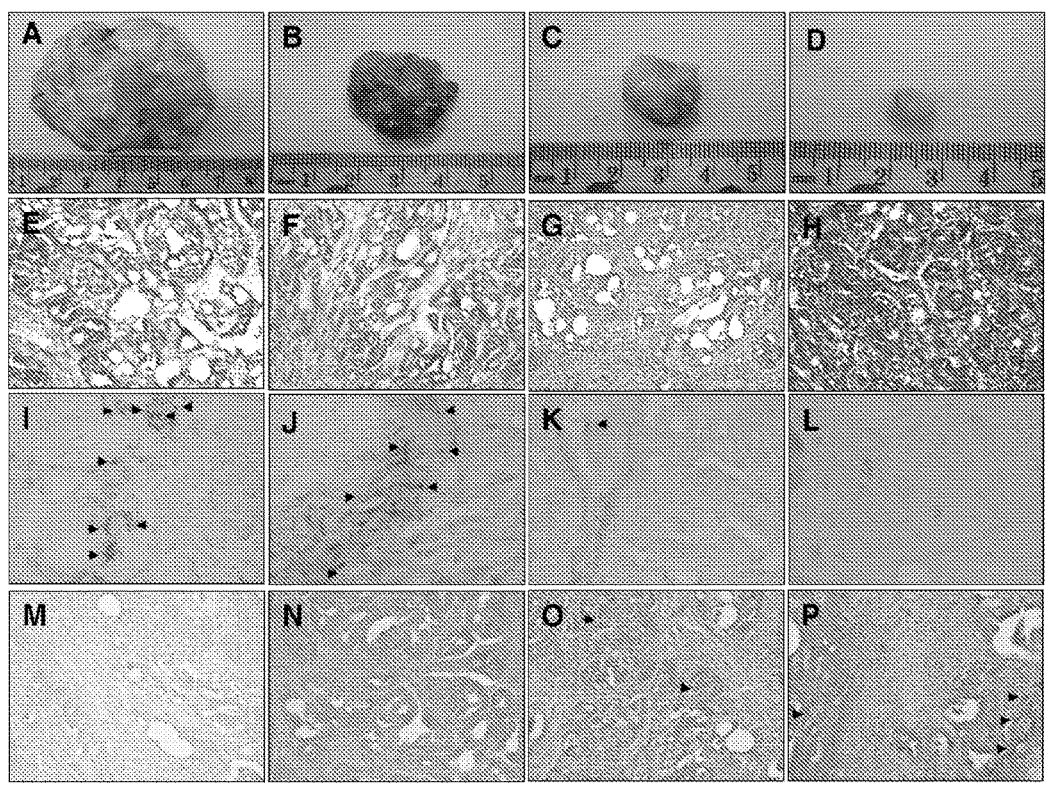
FIGS. 2A-2P. Chemoprevention of experimental rat mammary carcinogenesis by AMR-Me. Effects of AMR-Me on mammary tumorigenesis (FIGS. 2A-2D), histopathological profile (FIGS. 2E-2H), cell proliferation (FIGS. 2I-2L), and apoptosis (FIGS. 2M-2P). The rats were treated with oral AMR-Me (0.8, 1.2 or 1.6 mg/kg; three times a week) 2 weeks prior to and 16 weeks following DMBA administration. All animals were sacrificed 16 weeks following DMBA exposure. The mammary tumors were subjected to morphological observation as well Apoptosis was detected by DNA fragmentation assay. An-ow heads indicate immuno-positive cells. Various treatment groups are.

In rats treated with DMBA only, most of the tumors were large (FIG. 2A). Treatment of rats with AMR-Me at low dose (0.8 mg/kg) reduced the size of tumors in DMBA-exposed animals (FIG. 2B). A further decrease in the size of tumor was observed in animals given AMR-Me at medium dose (1.2 mg/kg) (FIG. 2C). The tumors from the high dose (1.6 mg/kg) AMR-Me plus DMBA group showed striking reduction in size compared to those from any other DMBA-administered animals (FIG. 2D).

Effect of AMR-Me on Mammary Tumor Histopathology

The administration of DMBA produced ductal hyperplasia characterized by marked proliferation in the lumen of mammary duct as evidenced from H&E staining of tumor tissue. The analysis of morphological characteristics of tumor section reveals alteration and enlargement of alveolus with cells arranged in cribriform pattern. The cellular architecture shows uniformly neoplastic ductal epithelial cells with nuclear pleomorphism, marked by nuclear enlargement, hyperchromatinization and clumping of chromatids (FIG. 2E). Although the low dose (0.8 mg/kg) of AMR-Me did not modify tumor histopathological features (FIG. 2F), a medium (1.2 mg/kg) (FIG. 2G) or high (1.6 mg/kg) dose of AMR-Me (FIG. 2H) exhibited a moderate and substantial improvement of cellular architecture in tumor tissue, respectively. The latter group showed almost normal ductal and alveolar structure of breast tissue with uniform epithelial cells and no signs of hyperplasia or abnormal proliferation (FIG. 2H).

Effects of AMR-Me on Tumor Cell Proliferation and Apoptosis

To determine whether AMR-Me affects cell proliferation in mammary tumors induced by DMBA, the expression of PCNA was analyzed by immunohistochemical technique in tumor sections originating from several experimental groups. The representative photomicrographs of immunohistochemical staining are shown in FIG. 2I-2L. Tumor samples from DMBA control animals showed an abundance of PCNA-positive cells (FIG. 2I), indicating active cell proliferation. Although a marginal reduction in the proliferation of tumor cells was observed in low dose AMR-Me group (FIG. 2J), a substantial inhibition of cell proliferation in medium (FIG. 2K) and high (FIG. 2L) dose of AMR-Me-treated group indicate antiproliferative potential of this compound.

Figure 3A:
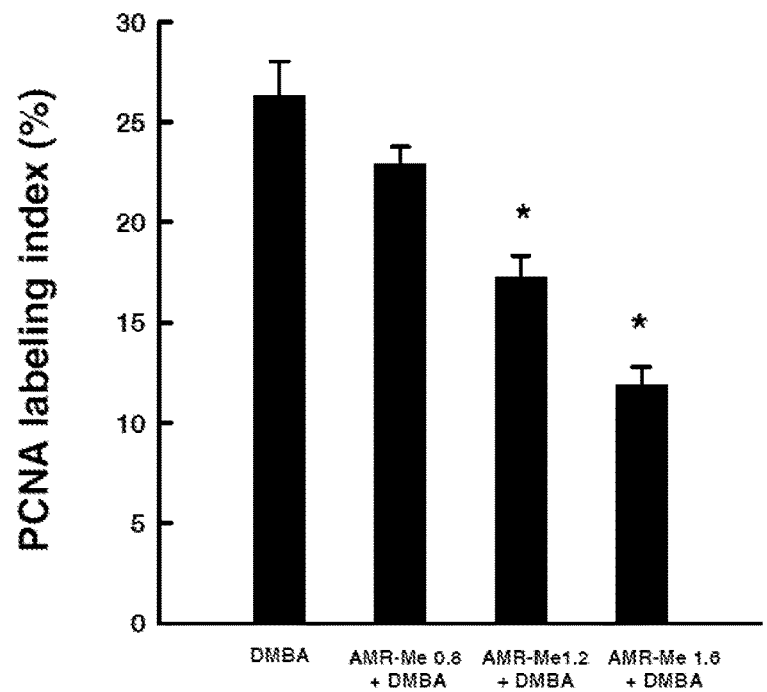
FIGS. 3A-3B. Quantitative analysis of tumor cell proliferation and apoptosis during DMBA mammary carcinogenesis in rats in the presence or absence of AMR-Me. Effects of AMR-Me on intra-tumor PCNA labeling index (LI) as determined by immunohistochemistry (FIG. 3A) and apoptotic index (AI) as measured by DNA fragmentation (FIG. 3B). The LI or AI was expressed as the number of immunopositive cells×100/total number of cells analyzed. Results are expressed as mean±SEM (n=4). *P<0.001 as compared to DMBA control.

As presented in FIG. 3A, the mean PCNA labeling index (LI) was found to be smaller in all AMR-Me treated animals. A statistically significant ($P<0.001$) decrease in PCNA LI was observed in medium or high dose AMR-Me group exposed to DMBA compared to DMBA control.

Figure 3B:
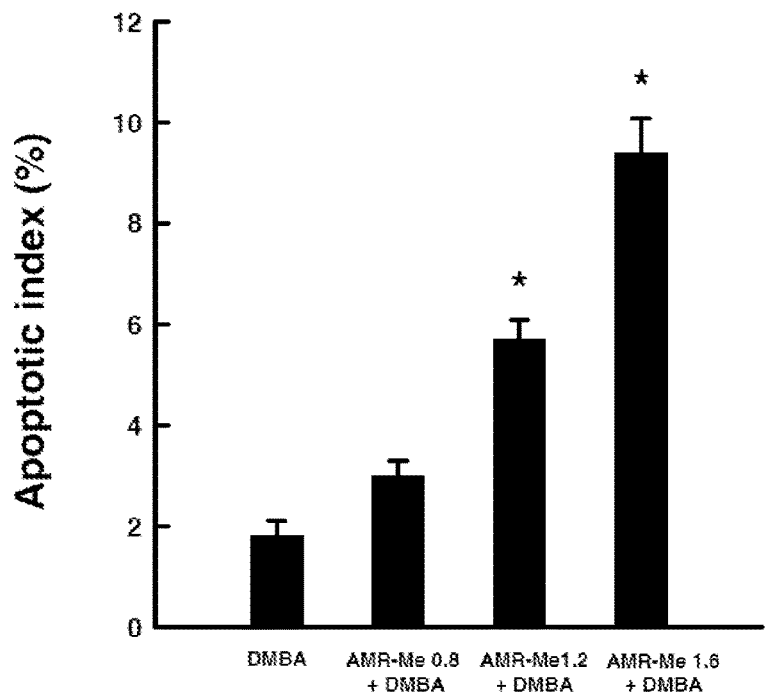

TdT-FragEL™ DNA fragmentation detection assay was used to investigate the extent of apoptosis in tumor samples. The chromagen-generated brown staining was used to identify apoptotic cells. While the presence of any positive staining was extremely rare in samples from DMBA control (FIG. 2M) or low dose AMR-Me plus DMBA group (FIG. 2N), a large number of brown staining overlapping the condensed chromatin of apoptotic bodies in medium (FIG. 2O) or high (FIG. 2P) dose AMR-Me plus DMBA group was observed. FIG. 3B illustrates the apoptotic index (AI) of each experimental group. While there were no noticeable difference in this index between two DMBA control and AMR-Me (low dose) plus DMBA group, there was a significant increase ($P<0.001$) in AI in tumor samples obtained from two experimental groups that received AMR-Me at medium or high dose compared to DMBA.

Effects of AMR-Me on Apoptosis-Related Gene Expressions

Figure 4A:
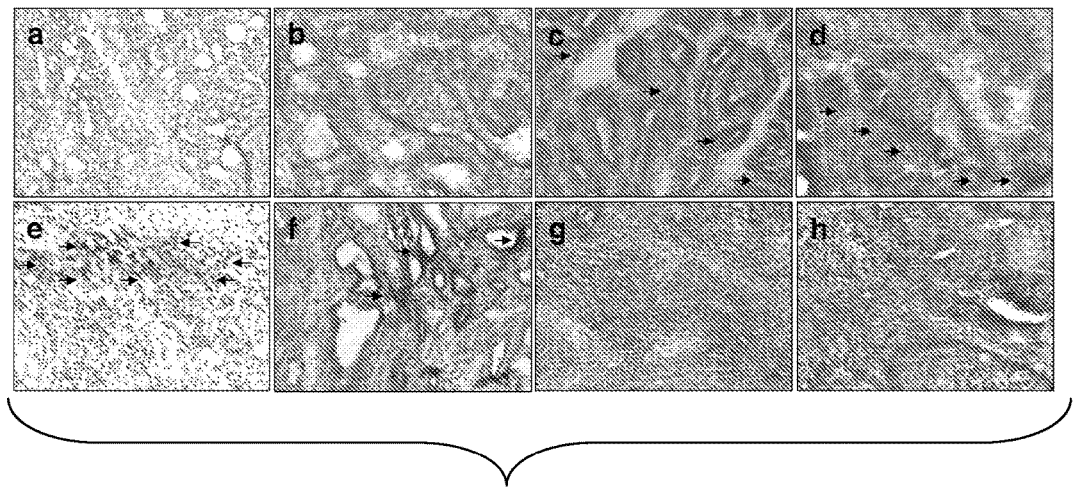
FIGS. 4A-4D. Effect of AMR-Me on protein expression of Bax and Bcl-2 in mammary tumors induced by DMBA in rats.
Figure 4B:
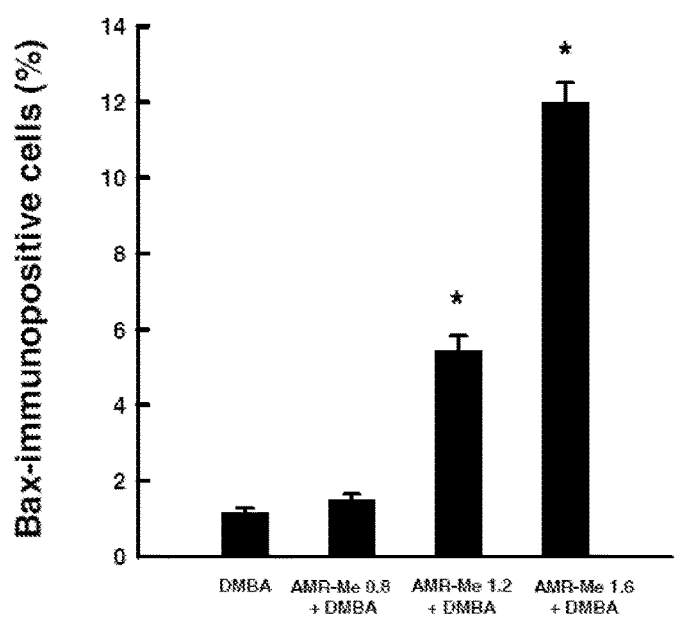
Figure 4C:
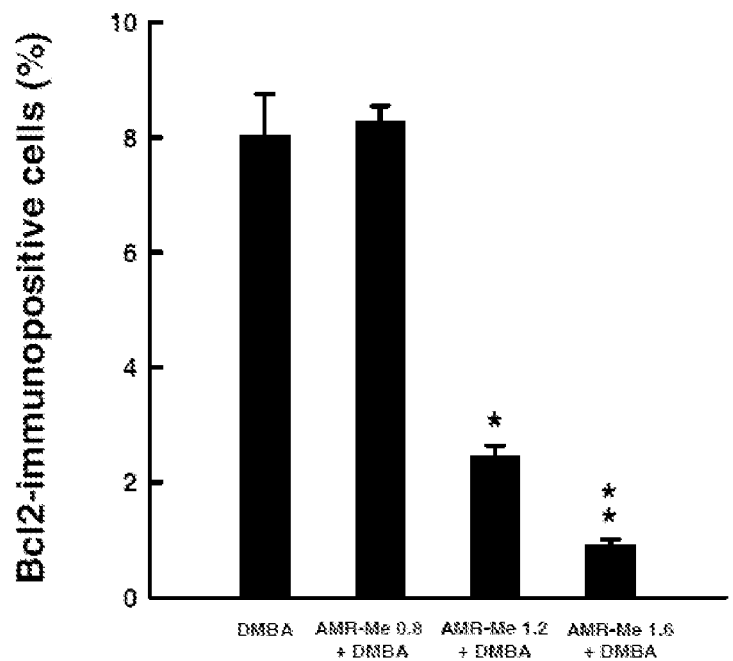
Figure 4D:
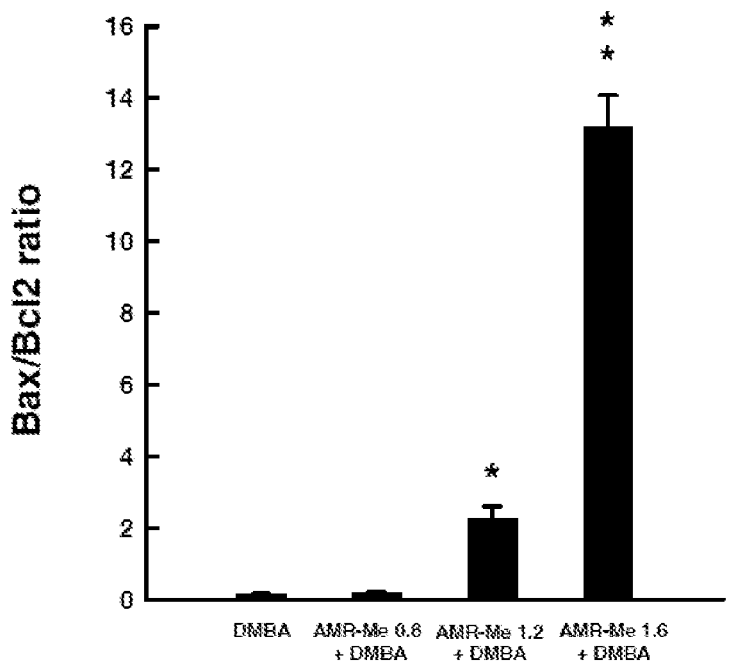

To investigate a possible mechanism of apoptosis induction by AMR-Me, the expression of the apoptosis-related proteins, namely Bax and Bcl-2, in mammary tumor sections was studied by immunohistochemical staining. The frequency of Bax-immunopositive cells was extremely low in tumors from DMBA-treated animals (FIG. 4A-a) or low dose of AMR-Me plus DMBA group (FIG. 4A-b). On the other hand, a dose-dependent increase in the expression of Bax was noticeable in the cytoplasm of tumor sections obtained from medium (FIG. 4A-c) or high dose of AMR-Me (FIG. 4A-d). These two doses of AMR-Me significantly ($P<0.001$) increased Bax-positive cells in DMBA-initiated rats compared to rats exposed to DMBA alone (FIG. 4B). Tumor sections from DMBA control animals exhibited substantial expression of cytoplasmic Bcl-2 (FIG. 4A-e) which was not altered by the low dose of AMR-Me (FIG. 4A-f). Other two doses of AMR-Me displayed considerable attenuation of Bcl-2 immunopositivity (FIG. 4A-g and FIG. 4A-h) with almost absence of Bcl-2 positive cells observed in the tumor tissue from animals treated with the highest dose (FIG. 4A-h). The quantitative analysis of Bcl-2-positive cells revealed a significant ($P<0.005$ or $0.001$) reduction in immunopositive cells in tumor samples from rats received medium or high dose of AMR-Me (FIG. 4C). Moreover, these two doses of AMR-Me elevated the Bax/Bcl-2 ratio in a dose-responsive manner (FIG. 4D). Nevertheless, a striking result ($P<0.001$) was obtained with the Bax/Bcl-2 ratio in the group that received the highest dose of AMR-Me compared to DMBA control.

Figure 5A:
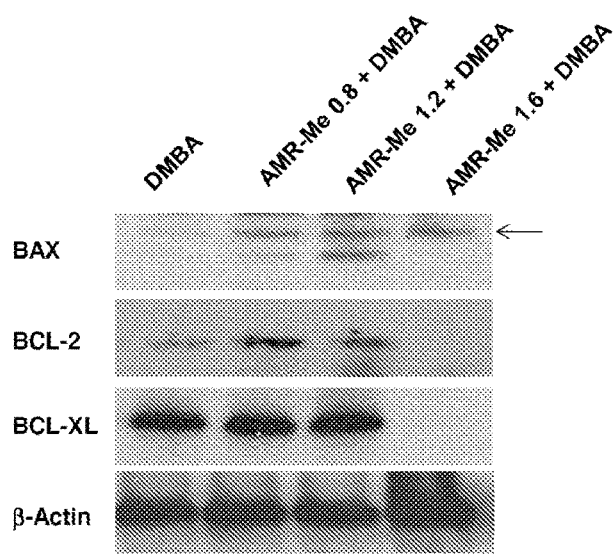
FIGS. 5A-5B. Effects of AMR-Me on the expression of anti- and pro-apoptotic genes in the tumors isolated from rats exposed to DMBA.
Figure 5B:
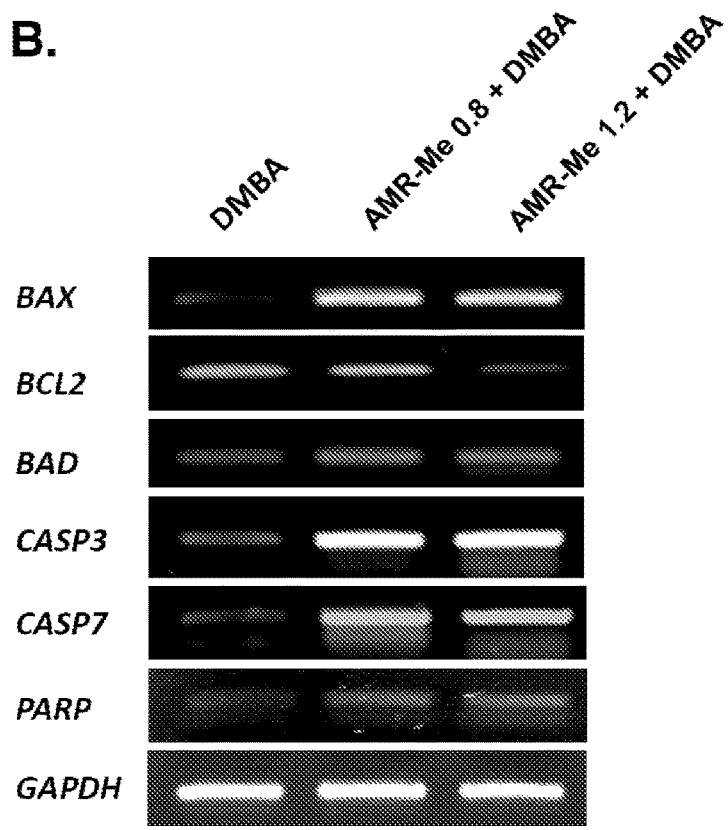

Tumor samples harvested from various experimental groups were used to perform Western blotting to confirm our immunohistochemical data on apoptosis-related proteins. As shown in Figure 5A, very limited expression of Bax was noticed in tumors separated from DMBA control animals. Pre- and post-treatment of AMR-Me at all doses elevated the Bax expression. In contrast, a considerable expression of Bcl-2 was observed in tumor tissue originated from DMBA control animals. Although treatment with AMR-Me at low or medium dose did not modify Bcl-2 expression, a complete abrogation in the expression of this protein was achieved with the high dose. Similar results were obtained with another protein, namely Bcl-XL. Figure 5B represents the gene expression data determining the mRNA levels of aforementioned as well as additional apoptosis-regulated genes. A clear up-regulation of BAX, BAD, CASP3, CASP7 and PARP and down-regulation of BCL2 represent the salient feature of the gene expression study. All these results explain mitochondrial pro-apoptotic mechanisms involved in AMR-Me-mediated prevention of mammary tumorigenesis.

Effects of AM R-Me on the Expressions of ERs

Figures 6A, 6B, 6C, 6D, 6E, 6F:
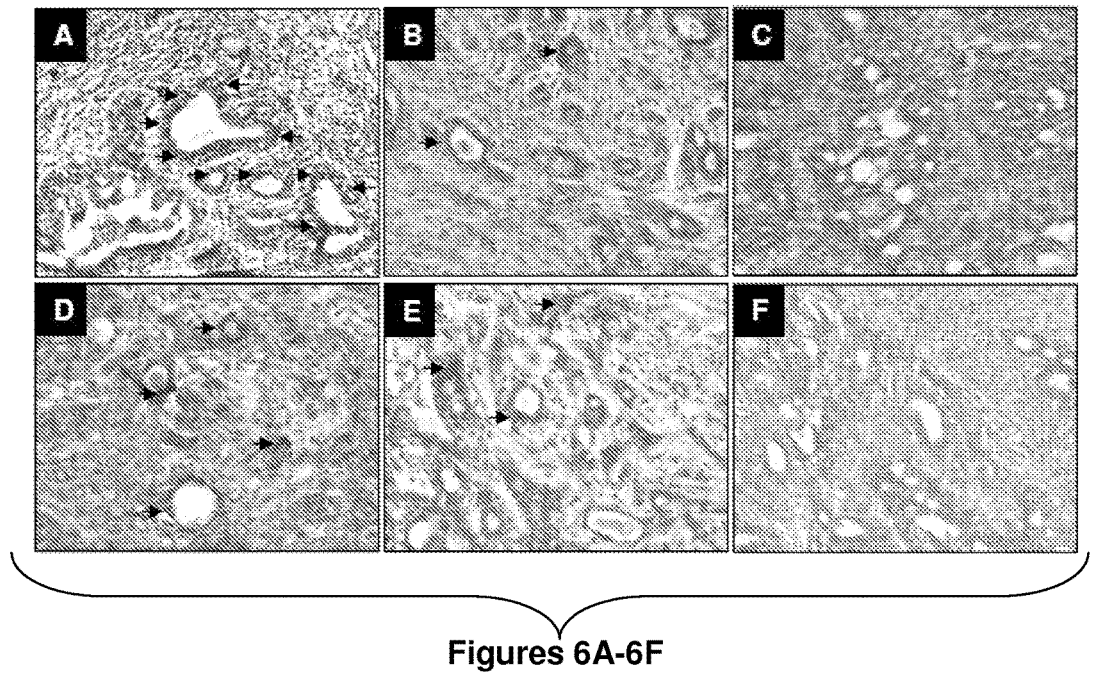
FIGS. 6A-6F. Effects of AMR-Me on the expression of estrogen receptor (ER)-a (FIGS. 6A-6C) and ER-13 (FIGS. 6D-6F) in mammary tumors induced by DMBA in rats. Various treatment groups are.
Figure 7A:
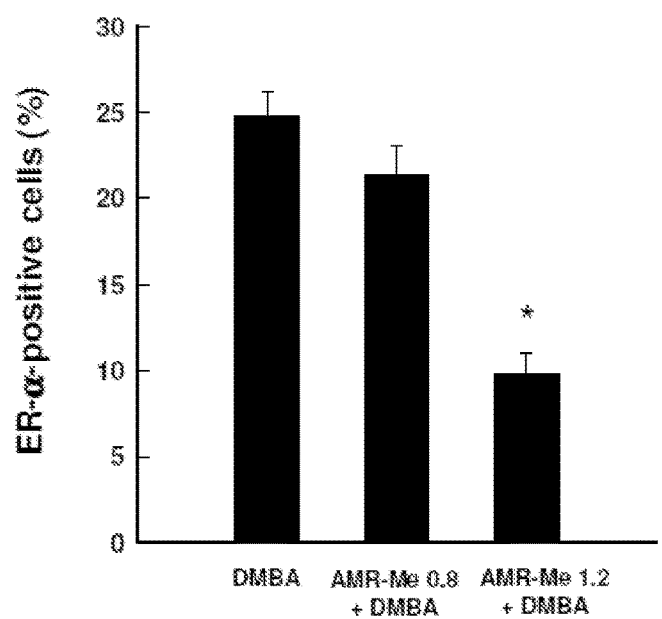
FIGS. 7A-7C. Quantitative analysis of ER-a-positive cells (FIG. 7A), ER-13-positive cells (FIG. 7B) and ER-a/ER-13 ratio (FIG. 7C). Each bar represents the mean±SEM (n=4).
Figure 7B:
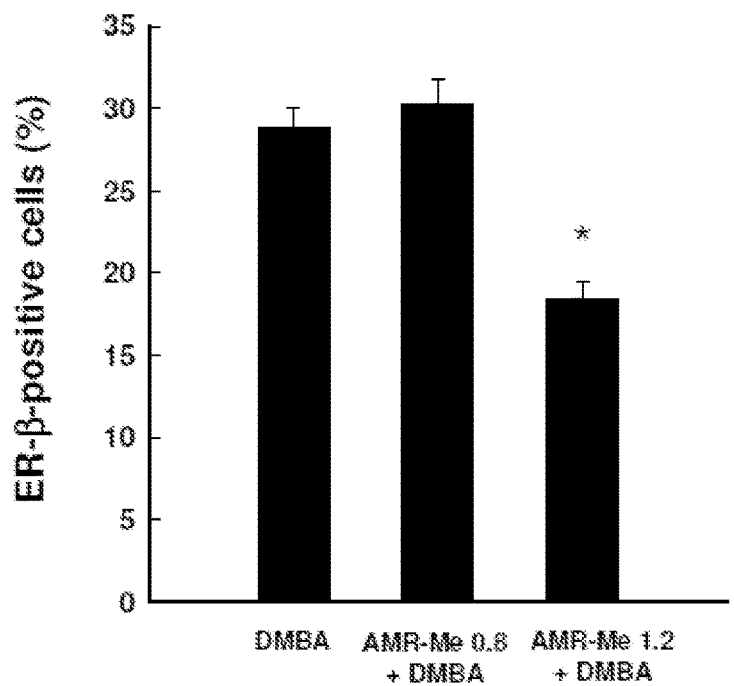
Figure 7C:
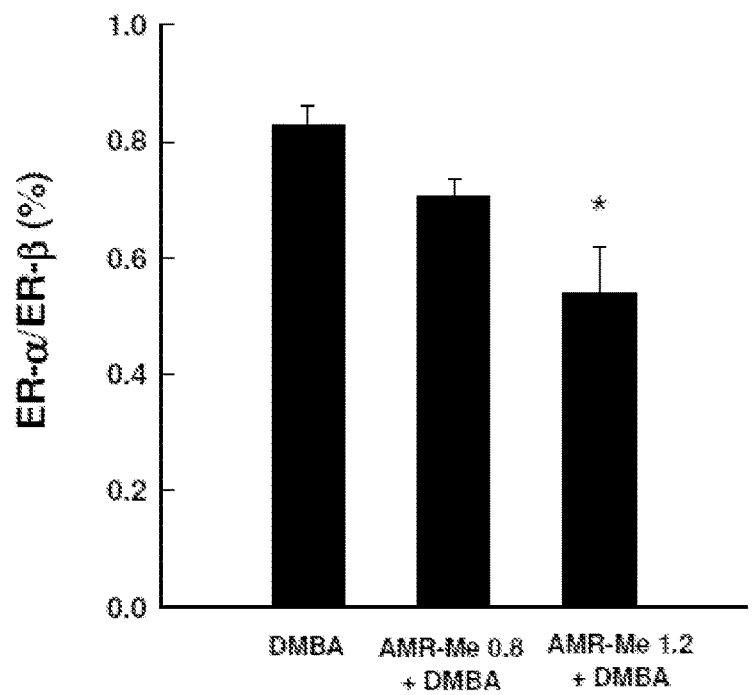
Figure 8:
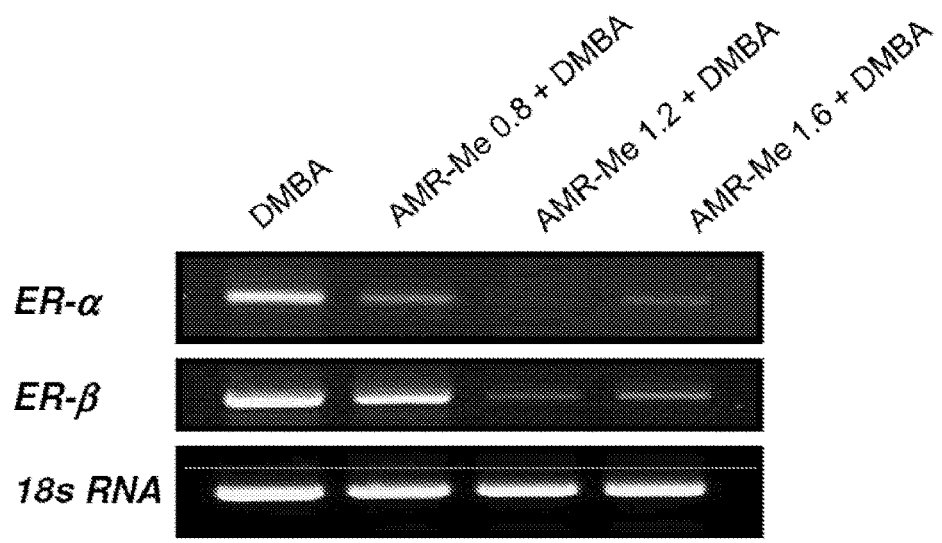
FIG. 8. Effect of AMR-Me on transcriptional expression of ER-a and ER-13 in DMBA-induced mammary tumors. Total RNA was isolated from tumor samples, subjected to reverse transcription, and resulting cDNA was subjected to RT-PCR analysis using specific primer sequence. The 18 s RNA was used as the housekeeping gene.

A substantial expression of ER-α was noticed in the tumor section obtained from DMBA control animals (FIG. 6A). This expression was reduced in tumors from animals treated with low (Figure B) or medium dose (FIG. 6C) of AMR-Me. A similar reduction in intra-tumor expression of ER-β was noticed in AMR-Me-exposed animals (FIGS. 6E and 6F). Quantitative analysis of immunohistochemical data revealed dose-dependent decrease in the number of ER-α (FIG. 7A) or ER-β-positive cells (FIG. 7B) with a concomitant drop in the ratio of ER-a/ER-β (FIG. 7C). The RT-PCR data (FIG. 8) confirmed the immunohistochemical finding.

Effect of AMR-Me on Cyclin DI Expression

Figures 9A, 9B, 9C, 9D:
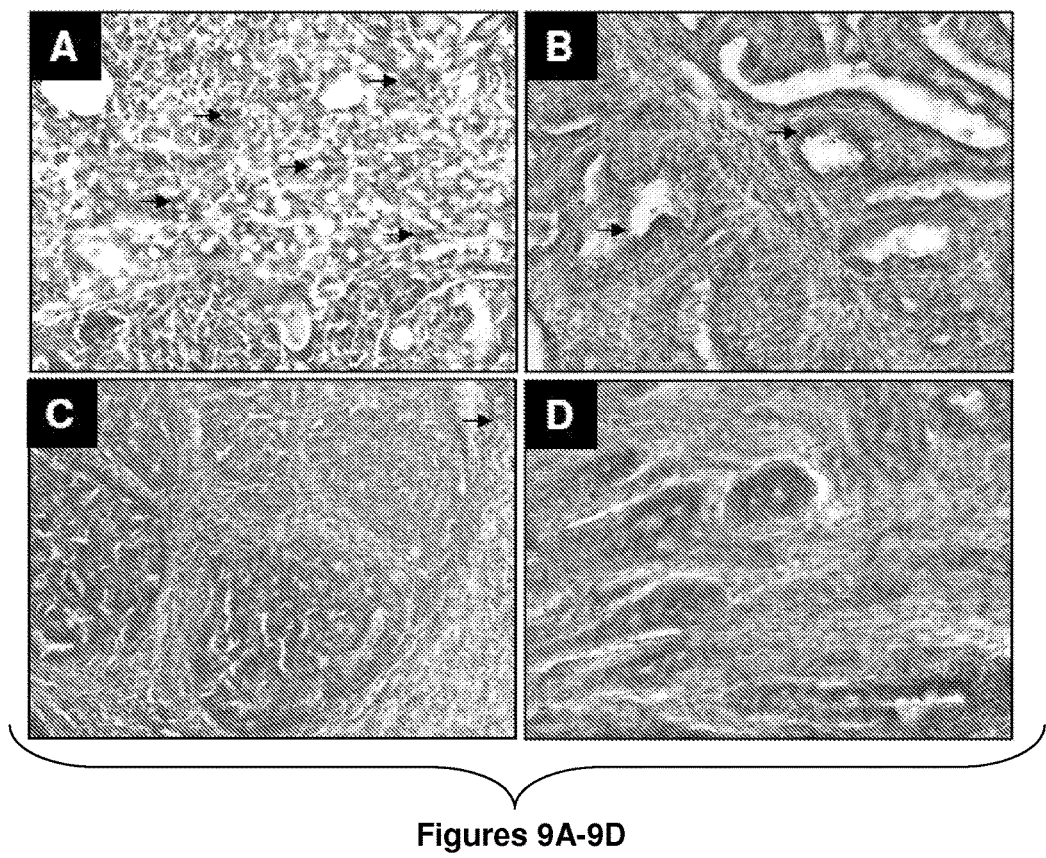
FIGS. 9A-9D. Effect of AMR-Me on the expression of cyclin D1 in mammary tumors induced by DMBA in rats. Various treatment groups are.
Figure 10:
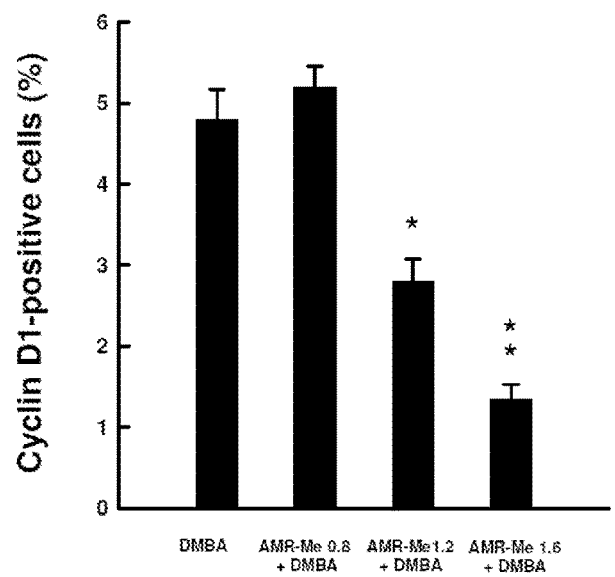
FIG. 10. Quantitative analysis of intra-tumor cyclin D1-positive cells. Each bar represents the mean±SEM (n=4). *P<0.05 and **P<0.001 as compared to DMBA control.

Represented in FIGS. 9A-9D are the immunocytochemical data depicting the expression of cell cycle specific gene cyclin D1 in tumor sections procured from several experimental animals. Cyclin D1 was found to be highly expressed in the DMBA control rats (FIG. 9A). A drastic reduction in the numbers of cyclin D1-immunoreactive cells were recorded in rats treated with medium (FIG. 9C) or high dose (FIG. 9O) of AMR-Me. The subsequent quantitative analysis performed denotes a significant ($P<0.05$ or $0.001$) decrease in the percentage of cyclin DI-positive cells in rats administered with either medium or high dose of AMR-Me with respect to DMBA control rats (FIG. 10).

Effect of AMR-Me on the Expression of β-Catenin

Figures 11A, 11B, 11C, 11D:
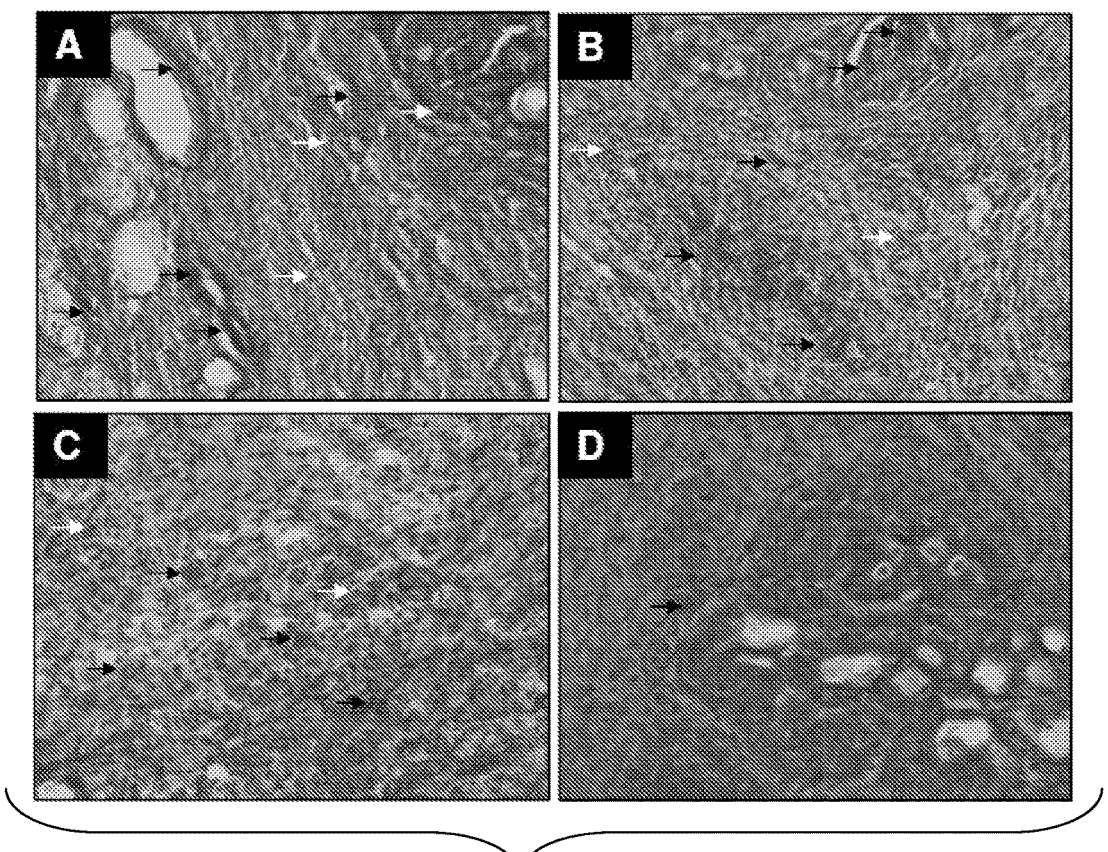
FIGS. 11A-11D. Effect of AMR-Me on the expression of β-catenin in mammary tumors induced by DMBA in rats. Various treatment groups are.
Figure 12A:
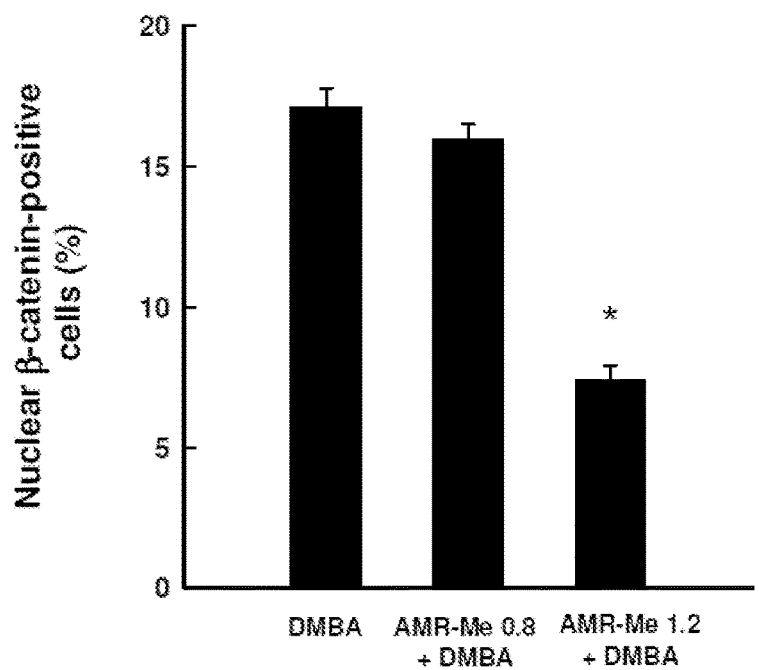
FIGS. 12A-12B. Quantitative analysis of nuclear (FIG. 12A) and cytoplasmic (FIG. 12B) β-catenin expression in rat mammary tumors. Each bar represents the mean±SEM (n=4). *P<0.001 as compared to DMBA control.
Figure 12B:
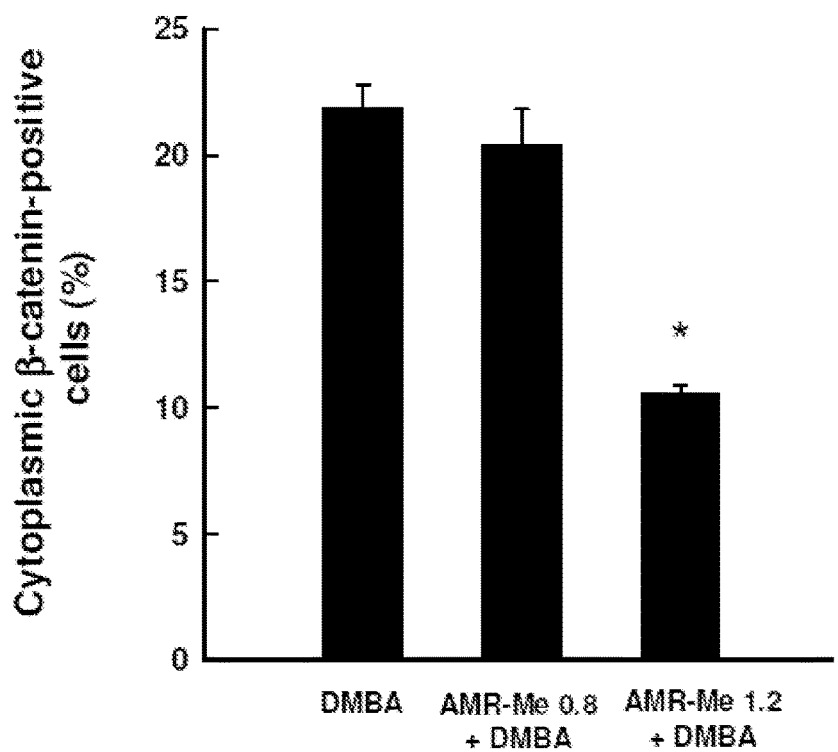
Figure 13:
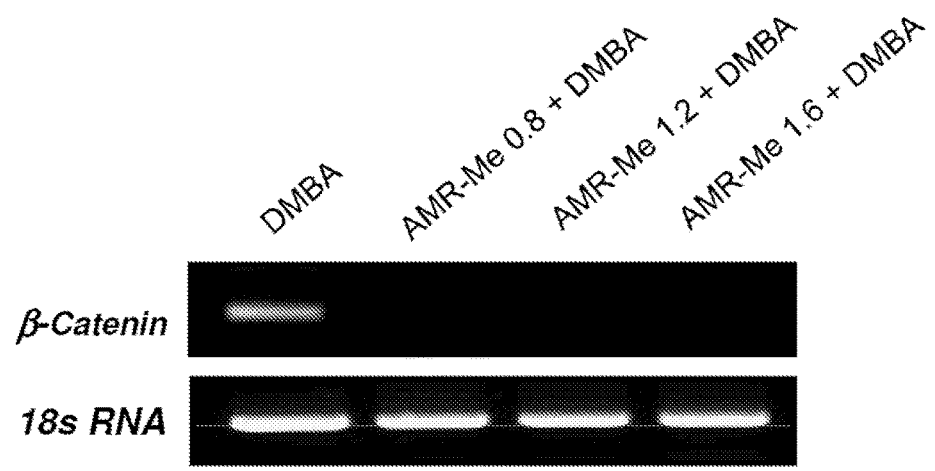
FIG. 13. Effect of AMR-Me on transcriptional expression of β-catenin in DMBA-induced mammary tumors. Total RNA was isolated from tumor samples, subjected to reverse transcription, and resulting cDNA was subjected to RT-PCR analysis using specific primer sequence. The 18 s RNA was used as the housekeeping gene.

Based on immunohistochemical analysis, variations in the nuclear and cytosolic expressions of β-catenin were clearly observed in tumor sections harvested from several groups of animals (FIGS. 11A-11D). Highly elevated frequency of both nuclear and cytosolic β-catenin-positive cells was recorded in rats exposed to DMBA (FIGS. 11A and 11B). In comparison, the rats treated with different doses of AMR-Me (0.8 mg/kg or 1.2 mg/kg) had decreased expression of nuclear as well as cytosolic expression of β-catenin (FIGS. 11C and 11D). The corresponding quantitative analysis presented in FIGS. 12A and 12B confirms our immunostaining data,
indicating a significant ($P<0.001$) decrease in nuclear and cytosolic β-catenin expression in AMR-Me-treated animals. Further confirmation of these results was shown utilizing RT-PCR technique (FIG. 13).

Toxicological Findings

Figures 14A, 14B, 14C, 14D:
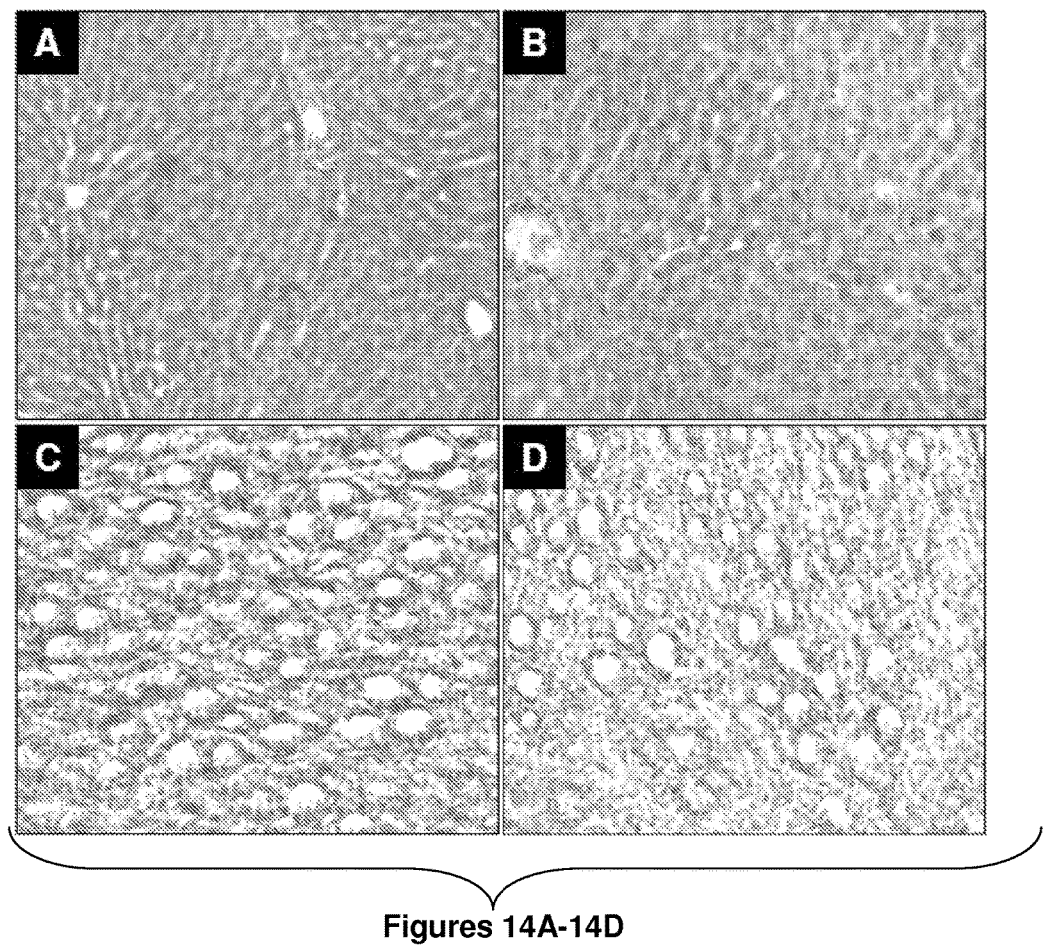
FIGS. 14A-14D. Effects of AMR-Me on hepatic (FIGS. 14A and 14B) and renal (FIGS. 14C and 14D) histopathological indices in rats. Various treatment groups are: (Figures A and C) normal control and (FIGS. 14B and 13D) AMR-Me (1.6 mg/kg body weight) control. Magnification: ×200.

The possible toxicity of high dose (1.6 mg/kg) of AMR-Me was studied by investigating hepatic and renal histopathological characteristics using H&E staining. As depicted in FIGS. 14A-14B, no hepatotoxicity was observed. Similarly, AMR-Me did not exhibit any nephrotoxicity in experimental animals (FIGS. 14C-14D).

DISCUSSION

The triterpenoid AMR-Me described herein exe is a remarkable chemopreventive activity against DMBA-induced mammary tumorigenesis in female Sprague-Dawley rats. Interestingly, breast tumor inhibitory effect of AMR-Me is achieved in a dose-responsive fashion during the 18-week study. While the low dose (0.8 mg/kg) reduces mammary carcinogenesis in statistically insignificant manner, the chemopreventive effect of medium (1.2 mg/kg) or high dose (1.6 mg/kg) is statistically significant and comparable. An inhibitory effect of AMR-Me has been clearly visualized by the reduced incidence of mammary tumors induced by DMBA. The observation of a significant lower percentage of rats with tumors following AMR-Me treatment can be explained in the virtue of the fact that the carcinogenic effect, even though initiated, was suppressed to a substantial extent.

The chemopreventive response of AMR-Me is reflected in the reduced total tumor burden as well as average tumor weight in DMBA-exposed animals. The observed tumor growth inhibitory effect of AMR-Me represents a selective toxic manifestation to proliferating cells in the light of the fact that these cells are rapidly proliferating compared to a relatively non-proliferative environment and thereby eventually suppress the development of breast cancer. The histopathological results reveal hyperplasia in rats exposed to DMBA and its reversal by AMR-Me treatment. Since there is a close connection between hyperplasia and subsequent steps leading to malignancy, the protective effect of AMR-Me against mammary carcinogenesis is a substantial suppression of the occurrence of hyperplasia, and thereby reduces the development of mammary tumors.

These in vivo results show a uniform and consistent growth of all experimental animal groups, as evident from similar body weight gains during the entire course of the experiment, this is an important aspect of AMR-Me function that shows the unaltered nutritional status of the treated animals. This is of importance since dietary restriction as well as nutritional deprivation resulting in body weight loss is implicated in the inhibition of tumor growth. Since these animals grew equally irrespective of specific treatment, it is now believed that the observed mammary tumor inhibitory effect of AMR-Me is not linked to an impairment of nutritional status of DMBA-initiated animals.

To investigate the mechanism by which AMR-Me inhibited mammary tumorigenesis, the extent of cell proliferation in tumors isolated from DMBA-exposed rats with or without AMR-Me treatment was examined. Cell proliferation is useful clinically for assessment of tumor prognosis because there is a relationship between proliferation and malignancy and for analysis of response of cancer cells to clinical interventions. Since cell proliferation plays a vital role in the progression of rat mammary gland tumorigenesis, agents that can affect tumor cell proliferation have immense value in chemoprevention of breast cancer. PCNA, a 36-kDa nuclear protein with functions as a cofactor of DNA polymerase 3, serves as an important proliferative marker in mammary carcinogenesis. The expression of PCNA was detected by an immunohistochemical technique. A substantially elevated expression of PCNA in mammary tumors of DMBA control animals is similar to the massive proliferation of tumor cells. The reduced expression of PCNA in conjunction with lower PCNA LI in tumor tissues of rats treated with AMR-Me strongly suggests antiproliferative mechanisms involved in the observed chemopreventive efficacy of this novel triterpenoid.

The programmed cell death, also known as apoptosis, is a fundamental form of physiological cell destruction driven by a distinct cellular mechanism characterized by cellular morphological alterations, chromatin condensation, DNA cleavage and generation of apoptotic bodies. The process of carcinogenesis selects against apoptosis to initiate, promote, and perpetuate the malignant phenotype. Thus, drug-induced apoptosis in tumors is a useful therapeutic and preventive strategy against cancer.

As described herein, intratumor apoptosis was evaluated by DNA fragmentation assay using an immunohistochemical technique to show the mechanism of suppression of tumor cell proliferation by AMR-Me. These results show a gradual increase in DNA fragmentation with increasing doses of AMR-Me indicating an increment in cell death.

These results also demonstrate apoptosis-inducing activity of AMR-Me in an experimental in vivo breast tumor model. The cellular machinery associated with apoptosis is highly conserved and mutations in genes that regulate apoptosis pathways, including Bcl-2 family members, are common in human cancers, and underscore the importance of apoptosis resistance in carcinogenesis. Several members of the Bcl-2 family which are overexpressed in a number of human malignancies (e.g., Bcl-2 and Bcl-xl) are known to block cell death, whereas other members (including Bax and Bad) are promoters of apoptosis with diminished levels found in several types of cancers. Thus, the inducing ability with an increase in the expression ratio between pro-apoptotic and anti-apoptotic and genes of Bcl-2 family is a factor in considering the efficacy of chemopreventive agents.

Using the immuno-histochemical analysis, it is now shown herein that continuous treatment with AMR-Me increased Bax expression and decreased Bcl-2 expression in mammary tumors with a resultant elevation of Bax/Bcl-2 ratio. This provides further evidence of the involvement of the members of Bcl-2 family in the induction of apoptosis during rat mammary carcinogenesis. In addition, the Western blot and RT-PCR data confirms the immuno-histochemical analysis and confirms Bcl-2 family proteins as targets of AMR-Me.

The pro- and anti-apoptotic members of the Bcl-2 family regulate mitochondrial membrane permealization, and thereby control the release of apoptotic factors from the mitochondrial intermembrane space. The release of cyt. c causes downstream initiation of caspase cascade by activating downstream effectors, such as caspase-3 and caspase-7, resulting in cleavage cascade of a variety of cellular proteins to facilitate apoptotic events.

The long-term treatment of DMBA-exposed rats with AMR-Me is successful in upregulating the transcriptional levels of caspase-3, caspase-7 and PARP in mammary tumors. While not wishing to be bound by theory, the inventor herein now believes that this accounts for the elevated apoptotic activities and the eventual inhibition of tumor growth. Also, the growth inhibitory and apoptosis-inducing activities of AMR-Me against breast cancer cells have been paralleled with increase in Bax and decrease in Bcl-2, cyt. c release, and subsequent induction of pro-caspase-9 and -7 and PARP cleavage These results demonstrate that triterpenoid AMR-Me exhibits a striking chemopreventive efficacy in DMBA classical animal model of breast cancer in a dose-responsive fashion. The chemopreventive effect of AMR-Me is shown by the ability of this compound to diminish the development of DMBA-induced mammary tumors and significantly reduce tumor burden.

Furthermore, these results show that breast tumor inhibitory effect of AMR-Me is achieved, at least in part, though interference with key hallmark capabilities of tumor cells, such as abnormal cell proliferation and evasion of apoptosis. Also, AMR-Me-mediated proapoptotic signal during experimentally-induced mammary carcinogenesis can be propagated through an upregulation of proapoptotic proteins and downregulation of antiapoptotic proteins of the mitochondrial apoptotic pathway.

All variables that modify the exposure to endogenous or exogenous estrogens are known to influence a woman's lifetime risk of developing breast cancer. It has been estimated that 70% of breast cancers express the ERs. Estrogen has been reported to enhance mammary tumor growth through ER-dependent cell proliferation. Carcinogen-induced tumors are ER positive and both ERα and ERβ) are believed to be associated with mammary cell proliferation and differentiation, and their modulation is believed to be important in carcinogenesis. Hence, it is important to determine whether there is expression of ERα and ERβ) in mammary carcinogenesis following AMR-Me treatment. Used herein were immunohistochemical as well as RT-PCR technique to monitor the expression of ER-α and ER-β in tumor tissues obtained from DMBA-exposed animals in the presence or absence of AMR-Me, A dose-dependent reduction in intra-tumor ER-α and ER-β expression as well as in the ratio of ER-α/ER-β in all AMR-Me-treated groups indicate less receptor sites for estrogen binging, resulting in diminished proliferation of tumor cells. The results based on the RT-PCR study supports the immuno-histochemical data. The modulation of ERs by AMR-Me as observed is now believed to be one of the principal mechanisms of action of chemoprevention of breast cancer by AMR-Me.

Cyclin D1, a cell cycle regulatory protein, is responsible for the transition from G1- to S-phase. As cyclin D1 possesses a critical role for cell cycle progression, dysregulated expression of cyclin D1 gene may contribute to cellular genomic instability and malignancy. Elevated expressions of cyclin D1 gene and protein disrupting G1/S regulatory point of the cell cycle have been found to lead abnormal cell proliferation during DMBA-induced mammary carcinogenesis in rats. Cyclin D1 can be used as a prognostic marker and therapeutic target. The results of the immunohistochemical analysis described herein clearly demonstrate an up-regulation of cyclin D1 protein expression in the tumors isolated from DMBA control animals. A significantly reduced of cyclin D1 expression was observed due to medium or high dose of AMR-Me treatment. Reversal of dysregulation of a critical checkpoint of the cell cycle is now believed to be one of the mechanisms of AMR-Me-mediated inhibition of mammary carcinogenesis and it underscores the value of targeting a cell cycle progression protein, such as cyclin D1, to achieve chemoprevention of mammary cancer.

The Wnt/β-catenin signaling pathway is implicated in regulation of various fundamental cellular events, including proliferation, differentiation, survival, inflammation, oxidative stress, morphogenesis and regeneration. In canonical Wnt pathway, the multifunctional protein β-catenin represents the key signaling intermediate. Under normal physiological conditions, free cytoplasmic β-catenin undergoes degradation through a coordinated action of a multiprotein destruction complex. In the event of Wnt ligands binding with the transmembrane Frizzled (FZD) receptor and co-receptor low-density lipoprotein receptor-related protein 5 or 6 (LRP 5/6), activation of the canonical Wnt pathway is initiated. The net result is the stabilization and accumulation of β-catenin in the cytosol followed by its translocation to the nucleus. Once inside the nucleus, β-catenin interacts with transcription factor T-cell factor/lymphoid enhancer factor and eventually activates the transcription of various Wnt target genes implicated in a number of important biological functions, including proliferation, cell cycle control (e.g., cyclin D1), apoptosis and inflammation. Aberant constitutive activation of the Wnt/β-catenin pathway leads to uncontrolled cell proliferation, growth and survival, promoting various human malignancies, including breast cancer. The immunohistochemical analysis described herein now shows that tumor cells from DMBA control animals exhibit a marked overexpression of β-catenin in the cytoplasm and/or nucleus, confirming activation of Wnt/β-catenin signaling pathway at an early stage of DMBA mammary carcinogenesis in rats. The accompanying RT-PCR data provide further support to the discovery regarding induction of the canonical Wnt/β-catenin pathway. A dose-dependent inhibition of β-catenin expression in transcriptional and translational levels by AMR-Me clearly underscores the impairment of the canonical Wnt/β-catenin oncogenic signaling in rat mammary carcinogenesis.

A significant aspect of these discoveries is that normal animals exposed to the highest dose (1.6 mg/kg body weight) of AMR-Me did not show evidence of toxicity following a chronic (18 weeks) exposure period, as evidenced by the unaltered food and water intakes, growth curve, and hepatic and renal histopathological indices. The absence of toxicity of AMR-Me in a mammalian species should be viewed favorably regarding long-term safety of ingestion of AMR-Me for achieving breast cancer chemoprevention in the human population.

Example 3

Methods of Making Analogs

FIG. 1B shows a formula representing the chemical structure of AMR analogs, wherein R is selected from an alkyl, alkenyl, alkynyl, aryl, arylalkyl containing halogen and alkoxy. In certain embodiment, R is Me.

The term "alkyl" can refer to a straight or branched chain alkyl moiety having from one to six carbon atoms, including for example, methyl, ethyl, propyl, isopropyl, butyl, tert-butyl, pentyl, hexyl and the like. The term "alkenyl" can refer to a straight or branched chain alkyl moiety having two to six carbon atoms and having in addition one double bond, of either E or Z stereochemistry where applicable. The term "alkenyl" includes for example, vinyl, 1-propenyl, 1- and 2-butenyl, 2-methyl-2-propenyl and the like. The term "alkynyl" can refer to a straight or branched chain alkyl moiety having two to six carbon atoms and having in addition one triple bond. The term "alkynyl" includes for example, ethynyl, 1-propynyl, 1- and 2-butynyl, 1-methyl-2-butynyl and the like. The term "aryl" can refer substituted phenyl. The term "arylalkyl" can refer substituted benzyl. The term "alkoxy" can refer to an alkyl-0-group, in which the alkyl group is as previously described. The term "alkoxy" can include a strain chain or branched alkoxy group containing a maximum of six carbon atoms, such as methoxy, ethoxy, propoxy, isopropoxy, butoxy, tert-butoxy, and the like. The term "halogen" means fluoro, chloro, bromo, or iodo.

As used herein, the term "analogs" refers to compounds which are substantially the same as another compound, but which may have been modified by, for example, adding side groups, oxidation or reduction of the parent structure. Chemical modifications can be accomplished by those skilled in the ailby protecting all functional groups present in the molecule and deprotecting them after carrying out the desired reactions. Analogs exhibiting the desired biological activity (such as induction of apoptosis, and/or cytotoxicity) can be identified or confirmed using cellular assays or other in vitro or in vivo assays.

Example 4

Methods for Treating a Disorder and/or Disease State

There is provided herein methods for treating, inhibiting, relieving or reversing a disorder and/or disease state response. In the methods described herein, an agent that interferes with a signaling cascade is administered to an individual in need thereof, such as, but not limited to, subjects in whom such complications are not yet evident and those who already have at least one such response.

In the former instance, such treatment is useful to prevent the occurrence of such response and/or reduce the extent to which they occur. In the latter instance, such treatment is useful to reduce the extent to which such response occurs, prevent their further development or reverse the response.

The AMR compounds are useful for both non-therapeutic and therapeutic purposes. The AMR compounds are effective for reducing proliferation in a target cell and/or reducing aberrant cell growth. Also, the AMR compounds are useful to reduce unwanted cell growth in different situations, including in vitro and in vivo.

Dosages and Dosage Schedules

The dosage regimen can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

Non-limiting examples of suitable dosages can include total daily dosage of between about 25-4000 mg/m$^2$ administered orally once-daily, twice-daily or three times-daily, continuous (every day) or intermittently (e.g., 3-5 days a week). For example, the compositions can be administered in a total daily dose, or divided into multiple daily doses such as twice daily, and three times daily.

Other non-limiting examples of suitable dosages and methods of administration can include the intravenous administration directly to the tumor site via a catheter.

In addition, the administration can be continuous, i.e., every day, or intermittently. The terms "intermittent" or "intermittently" as used herein means stopping and starting at either regular or irregular intervals. For example, intermittent administration may be administration one to six days per week or it may mean administration in cycles (e.g., daily administration for two to eight consecutive weeks, then a rest period with no administration for up to one week) or it may mean administration on alternate days.

In addition, the compositions may be administered according to any of prescribed schedules, consecutively for a few weeks, followed by a rest period. For example, the composition may be administered according to any one of the prescribed schedules from two to eight weeks, followed by a rest period of one week, or twice daily at a dose for three to five days a week.

It should be apparent to a person skilled in the art that the various dosages and dosing schedules described herein merely set forth specific embodiments and should not be construed as limiting the broad scope of the invention. Any permutations, variations and combinations of the dosages and dosing schedules are included within the scope of the present invention.

Pharmaceutical Compositions

While AMR and AMR analog compounds can be administered as isolated compounds, in certain embodiments, in certain embodiments, it may be preferred to administer these compounds as a pharmaceutical composition. Thus, also within the contemplated scope of the present invention are pharmaceutical compositions comprising AMR, or an analog thereof, as an active agent, or physiologically acceptable salt(s), solvate(s), hydrate(s) and the like thereof, in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The AMR compounds and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds described herein, and a pharmaceutically acceptable carrier. Preferably, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

The pharmaceutical compositions can be administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field. In certain embodiments, preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Non-limiting examples of solid carriers/diluents include a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Non-limiting examples of liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20®, Tween 80®, Pluronic F68®, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal®, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In certain embodiments, the active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For example, the compounds may be administered intravenously on the first day of treatment, with oral administration on the second day and all consecutive days thereafter. The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound or formulation administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM.

In another embodiment, the concentration of the compound in the patient's plasma is maintained at ranges between about 10 to about 50 nM. The optimal amount of the compound that should be administered to the patient in the practice of the present invention will depend on the particular compound used and the type of cancer being treated.

Uses in Combination with Other Therapeutics

The therapeutic methods and compositions invention can be advantageously combined with at least one additional therapeutic method, including but not limited to chemotherapy, radiation therapy, or any other therapy known to those of skill in the art for the treatment and management of proliferation disorders (e.g., cancer), such as administration of an anti-cancer agent.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method for synthesizing 25-Hydroxy-3-oxoolean-12-en-28-oic Acid with chemical Structure

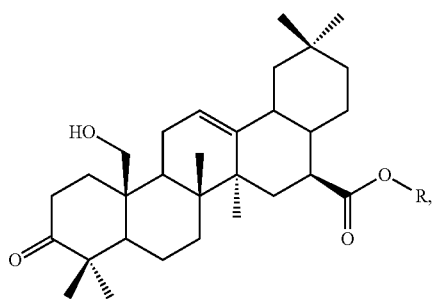

comprising the steps of:

(a) conducting a Jones oxidation of oleanolic acid with chemical structure

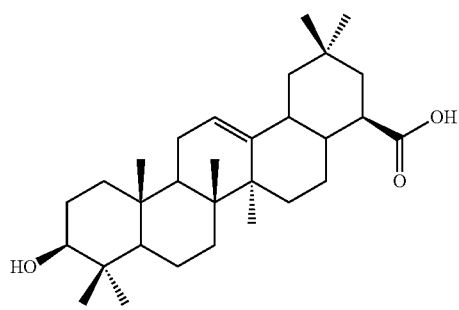

by adding a Jones reagent solution to the oleanolic acid suspended in $CH_3COCH_3$, and $CHCl_3$ or $CH_2Cl_2$, and then adding i-PrOH, $H_2O$, and $CH_2Cl_2$, and then concentrating Jones oxidation organic layer to obtain 3-Oxoolean-12-en-28-oic Acid with chemical structure

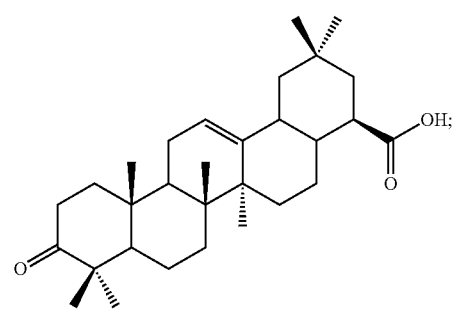

(b) adding benzyl chloride and $K_2CO_3$ to a solution of the 3-Oxoolean-12-en-28-oic acid in dioxane, and then removing solids from dioxane layer, and then concentrating the dioxane layer to obtain 3-Oxoolean-12-en-28-oic Acid Benzyl Ester with chemical structure

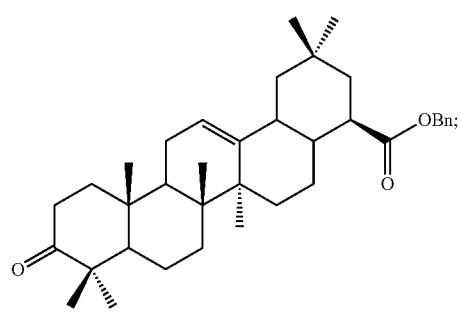

(c) refluxing a suspension of the 3-Oxoolean-12-en-28-oic Acid Benzyl Ester, toluene, ethylene glycol, and p-toluenesulfonic acid with azeotropic removal of water, and then washing resulting mixture with aqueous $NaHCO_3$, and then concentrating resulting organic layer to obtain 3-(10,30-Dioxolane)olean-12-en-28-oic Acid Benzyl Ester with chemical structure

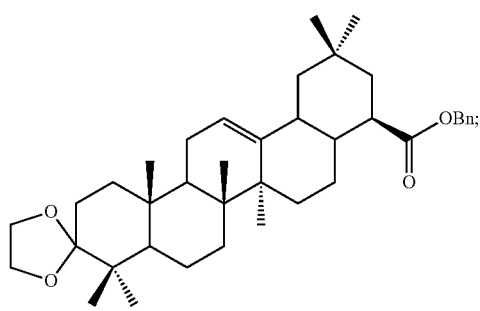

(d) oxidizing the 3-(10,30-Dioxolane)olean-12-en-28-oic Acid Benzyl Ester by adding $NaIO_4$, $Bu_4NBr$, and $RuCl_3$ to the 3-(10,30-Dioxolane)olean-12-en-28-oic Acid Benzyl Ester dissolved in $CCl_4$ and $H_2O$, and then concentrating filtered organic layer to obtain 3-(10,30-Dioxolane)olean-11-oxo-12-en-28-oic Acid Benzyl Ester with chemical structure

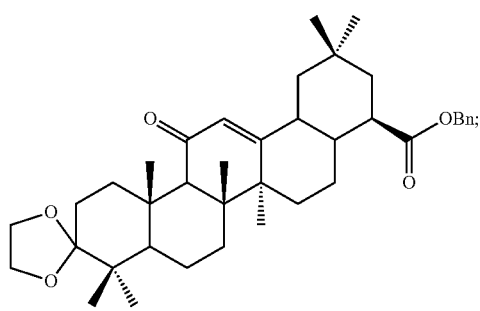

(e) adding sodium triethylborohydride in THF to the 3-(10,30-Dioxolane)olean-11-oxo-12-en-28-oic Acid Benzyl Ester dissolved in dry THF, and then adding H₂O, and then extracting with EtOAc, and then concentrating EtOAc extract to obtain 3-(10,30-Dioxolane)olean-11β-hydroxy-12-en-28-oic Acid Benzyl Ester with chemical structure

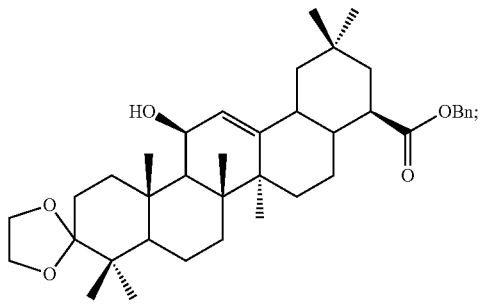

(f) adding nitrosyl chloride to the 3-(10,30-Dioxolane) olean-11β-hydroxy-12-en-28-oic Acid Benzyl Ester in pyridine, and then pouring mixture into ice-water to form a suspension, and then extracting the suspension with EtOAc, and then concentrating the EtOAc extract to obtain a nitrite compound with chemical structure

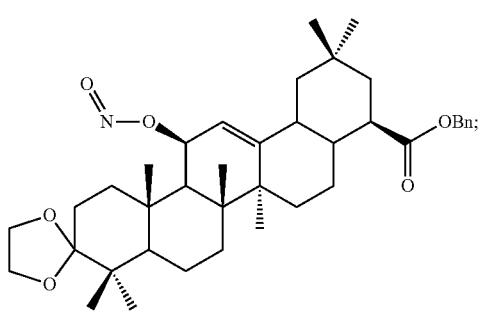

(g) irradiating the nitrite compound in dry toluene under a nitrogen atmosphere with a high pressure mercury lamp to obtain an aldoxime compound with chemical structure in toluene;

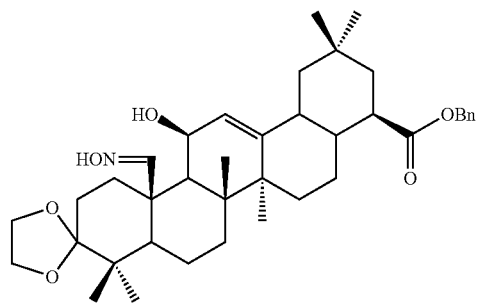

(h) removing the toluene in vacuo from the aldoxime compound, and then treating the aldoxime compound in a mixture of dioxane, water, and acetic acid, to sodium nitrite in water to form an aldehyde compound and a hemiacetal compound in the mixture, and then extracting the mixture with EtOAc and washing the EtOAC extract with saturated aqueous NaHCO₃, and then concentrating the EtOAc extract to obtain the aldehyde compound and the hemiacetal compound;

(i) adding NaBH₄ in MeOH to the aldehyde compound and hemiacetal compound dissolved in CHCl₃, and then concentrating organic layer to obtain 3-(10,30-Dioxolane)olean-11β,25-dihydroxy-12-en-28-oic Acid Benzyl Ester with chemical structure

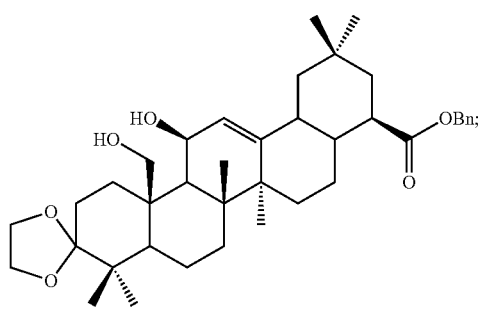

(j) treating the 3-(10,30-Dioxolane)olean-11β,25-dihydroxy-12-en-28-oic Acid Benzyl Ester in a CHCl₃ and pyridine solution with acetic anhydride, and then washing the pyridine and CHCl₃ layer with aqueous NaHCO₃ and then concentrating the organic layer to obtain 3-(10,30-Dioxolane)olean-11β-hydroxy-25-acetoxy-12-en-28-oic Acid Benzyl Ester chemical structure

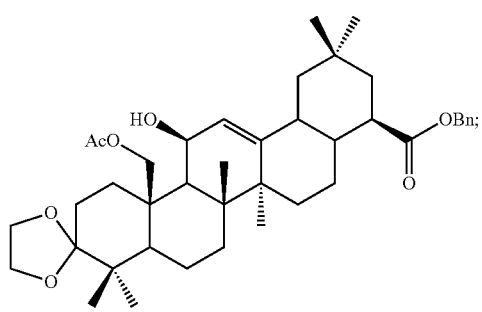

(k) hydrogenating the 3-(10,30-Dioxolane)olean-11β-hydroxy-25-acetoxy-12-en-28-oic Acid Benzyl Ester dissolved in NaHCO₃-treated EtOH with 10% palladium on charcoal catalyst and then concentrating filtered reaction mixture to obtain a residue;

(l) treating the residue with 30% TFA in CH$_2$Cl$_2$, and then adding saturated aqueous NaHCO$_3$, and then extracting with EtOAc and concentrating the EtOAc extract to obtain 3-Oxo-25-acetoxy-olean-12-en-28-oic Acid with chemical structure

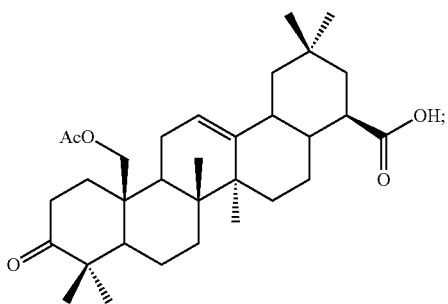

and (m) heating under reflux a mixture of the 3-Oxo-25-acetoxy-olean-12-en-28-olic Acid in methanol, with KOH in water or with NaOH in water, and then acidifying the mixture to form the 25-Hydroxy-3-oxoolean-12-en-28-oic Acid, and then extracting the mixture with EtOAc and then concentrating the EtOAc extract to obtain the 25-Hydroxy-3-oxoolean-12-en-28-oic Acid.

2. The method according to claim 1, further comprising the step of:

(n) treating a solution of the 25-Hydroxy-3-oxoolean-12-en-28-oic Acid in ethyl ether with diazomethane, and then destroying excess diazomethane with acetic acid, and then washing resulting ethyl ether solution with a NaHCO$_3$ solution, and then concentrating the ethyl ether solution to obtain 25-Hydroxy-3-oxoolean-12-en-28-oic Acid Methyl Ester with chemical structure

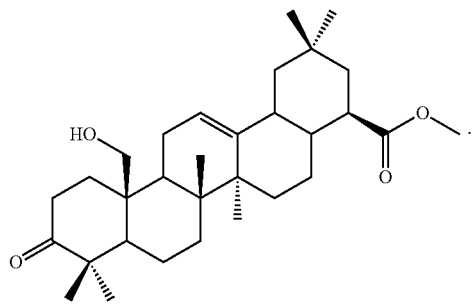

3. The method according to claim 1, wherein at step (a) the Jones reagent solution is added to the Oleanolic acid in the CH$_3$COCH$_3$, and the CH$_2$Cl$_2$.

4. The method according to claim 1, wherein at step (a) the Jones reagent solution is added to the Oleanolic acid in the CH$_3$COCH$_3$, and the CHCl$_3$.

5. The method according to claim 1, wherein at step (a) wherein the Jones oxidation of the oleanolic acid is conducted at a temperature at 5° C.

6. The method according to claim 1, further comprising at step (a) purifying the 3-Oxoolean-12-en-28-oic Acid by a crystallization of the 3-Oxoolean-12-en-28-oic Acid in methanol.

7. The method according to claim 1, further comprising at step (b) refluxing mixture of the benzyl chloride, the K$_2$CO$_3$ and the 3-Oxoolean-12-en-28-oic acid in the dioxane before removing the solids from the dioxane layer.

8. The method according to claim 1, further comprising at step (b) crystallizing the 3-Oxoolean-12-en-28-oic Acid Benzyl Ester in CHCl$_3$ and MeOH.

9. The method according to claim 1, wherein at step (c) a Dean-Stark apparatus is used for for the azeotropic removal of water during the refluxing of the suspension of the 3-Oxoolean-12-en-28-oic Acid Benzyl Ester, toluene, ethylene glycol, and p-toluenesulfonic acid.

10. The method according to claim 1, further comprising at step (c) crystallizing the 3-(10,30-Dioxolane)olean-12-en-28-oic Acid Benzyl Ester in CHCl$_3$ and MeOH.

11. The method according to claim 1,
wherein at step (d) 0.06 molar:0.3 molar is the molar ratio of the 3-(10,30-Dioxolane)olean-12-en-28-oic Acid Benzyl Ester to the NaIO$_4$, and
wherein at step (d) 0.06 molar:0.12 molar is the molar ratio of the 3-(10,30-Dioxolane)olean-12-en-28-oic Acid Benzyl Ester to the RuCl$_3$.

12. The method according to claim 1, further comprising at step (d) using saturated aqueous NaCl to wash the filtered organic layer before concentrating the filtered organic layer to obtain the 3-(10,30-Dioxolane)olean-11-oxo-12-en-28-oic Acid Benzyl Ester.

13. The method according to claim 1, further comprising at step (d) crystallizing the 3-(10,30-Dioxolane)olean-11-oxo-12-en-28-oic Acid Benzyl Ester in CHCl$_3$ and MeOH.

14. The method according to claim 1, wherein at step (e) the 3-(10,30-Dioxolane)olean-12-en-28-oic Acid Benzyl Ester is dissolved in dry −15° C. THF.

15. The method according to claim 1, further comprising at step (e) using aqueous NaCl to wash the EtOAc extract before concentrating the EtOAc extract to obtain the 3-(10,30-Dioxolane)olean-11β-hydroxy-12-en-28-oic Acid Benzyl Ester.

16. The method according to claim 1 further comprising at step (e) using a silica gel chromatography with hexane and acetone to purify the 3-(10,30-Dioxolane)olean-11β-hydroxy-12-en-28-oic Acid Benzyl Ester.

17. The method according to claim 1 wherein at step (f) the nitrosyl chloride is generated from NaNO$_2$ and HCl.

18. The method according to claim 1 wherein at step (f) the nitrosyl chloride is added to a solution of the 3-(10,30-Dioxolane)olean-11β-hydroxy-12-en-28-oic Acid Benzyl Ester in pyridine at −35° C.

19. The method according to claim 1 wherein at step (g) the irradiating of the nitrite compound occurs at a room temperature.

20. The method according to claim 1 wherein at step (h) the treating of the aldoxime compound in the mixture of dioxane, water, and acetic acid, to the sodium nitrite in water occurs at 0° C.

21. The method according to claim 1 further comprising at step (i) using a silica gel chromatography with hexane and acetone to purify the 3-(10,30-Dioxolane)olean-11β,25-dihydroxy-12-en-28-oic Acid Benzyl Ester.

22. The method according to claim 1 wherein step (j) at the treating of the 3-(10,30-Dioxolane)olean-11β,25-dihydroxy-12-en-28-oic Acid Benzyl Ester in the CHCl$_3$ and pyridine solution with the acetic anhydride occurs at a room temperature.

23. The method according to claim 1 further comprising at step (j) using a silica gel chromatography with hexane and acetone to purify the 3-(10,30-Dioxolane)olean-11β-hydroxy-25-acetoxy-12-en-28-oic Acid Benzyl Ester.

24. The method according to claim 1 wherein at step (k) the hydrogenating of the 3-(10,30-Dioxolane)olean-11β-hydroxy-25-acetoxy-12-en-28-oic Acid Benzyl Ester dissolved in NaHCO$_3$-treated EtOH with 10% palladium on charcoal catalyst occurs at a room temperature.

25. The method according to claim 1 further comprising at step (l) purifying the 3-Oxo-25-acetoxy-olean-12-en-28-oic Acid by a silica gel chromatography using petroleum ether and acetone.

26. The method according to claim 1 wherein at step (m) aqueous HCl is used for acidifying the mixture after the heating under reflux.

27. The method according to claim 1 further comprising at step (m) washing the EtOAc extracts with saturated aqueous NaCl and drying the washed EtOAc extracts over MgSO$_4$ before concentrating the EtOAc extracts to obtain the 25-Hydroxy-3-oxoolean-12-en-28-oic Acid.

28. The method according to claim 1, further comprising at step (m) purifying the 25-Hydroxy-3-oxoolean-12-en-28-oic Acid by a silica gel chromatography using hexane and acetone.

29. The method according to claim 2 wherein the esterifying of the 25-Hydroxy-3-oxoolean-12-en-28-oic Acid occurs in the ethyl ether cooled to 0° C.

30. The method according to claim 2 further comprising purifying the 25-Hydroxy-3-oxoolean-12-en-28-oic Acid Methyl Ester by a silica gel chromatography using petroleum ether and acetone.

\* \* \* \* \*